United States Patent [19]

Kropf

[11] Patent Number: 5,735,459

[45] Date of Patent: Apr. 7, 1998

[54] METHOD FOR FORMING AND APPLYING BIOLOGICAL CONTROL SYSTEM

[75] Inventor: Walter K. Kropf, Harrisburg, Oreg.

[73] Assignee: Smucker Manufacturing, Inc., Harrisburg, Oreg.

[21] Appl. No.: 494,163

[22] Filed: Jun. 23, 1995

[51] Int. Cl.$^6$ .................................................. B05B 9/00
[52] U.S. Cl. ........................ 239/8; 239/77; 239/144; 239/172; 47/1.01
[58] Field of Search ....................... 239/77, 144, 151, 239/170, 171, 172; 47/1.01

[56] References Cited

U.S. PATENT DOCUMENTS

| | | | |
|---|---|---|---|
| 2,738,226 | 3/1956 | Bals | 239/77 |
| 4,260,108 | 4/1981 | Maedgen, Jr. | 239/171 |
| 4,439,488 | 3/1984 | Trimnell et al. | 428/402.24 |
| 5,061,697 | 10/1991 | Shasha et al. | 514/60 |

FOREIGN PATENT DOCUMENTS 1116467  12/1959  Germany ............................ 239/77

*Primary Examiner*—Andres Kashnikow
*Assistant Examiner*—Steven J. Ganey
*Attorney, Agent, or Firm*—Marger Johnson McCollom & Stolowitz, P.C.

[57] ABSTRACT

This invention is directed to a bio-carrier which is non-toxic to most biological agents, will suspend various agents for increased uniformity of delivery, has adjustable adhesive properties which simulates nature, has variability in its adhesives and suspension qualities, it decreases control agent mortality, and it enhances overall effectiveness by allowing more live control agent to reach the target. It does so by depositing, adhering and maintaining the control agent in the active use zone of the target crop.

17 Claims, 18 Drawing Sheets

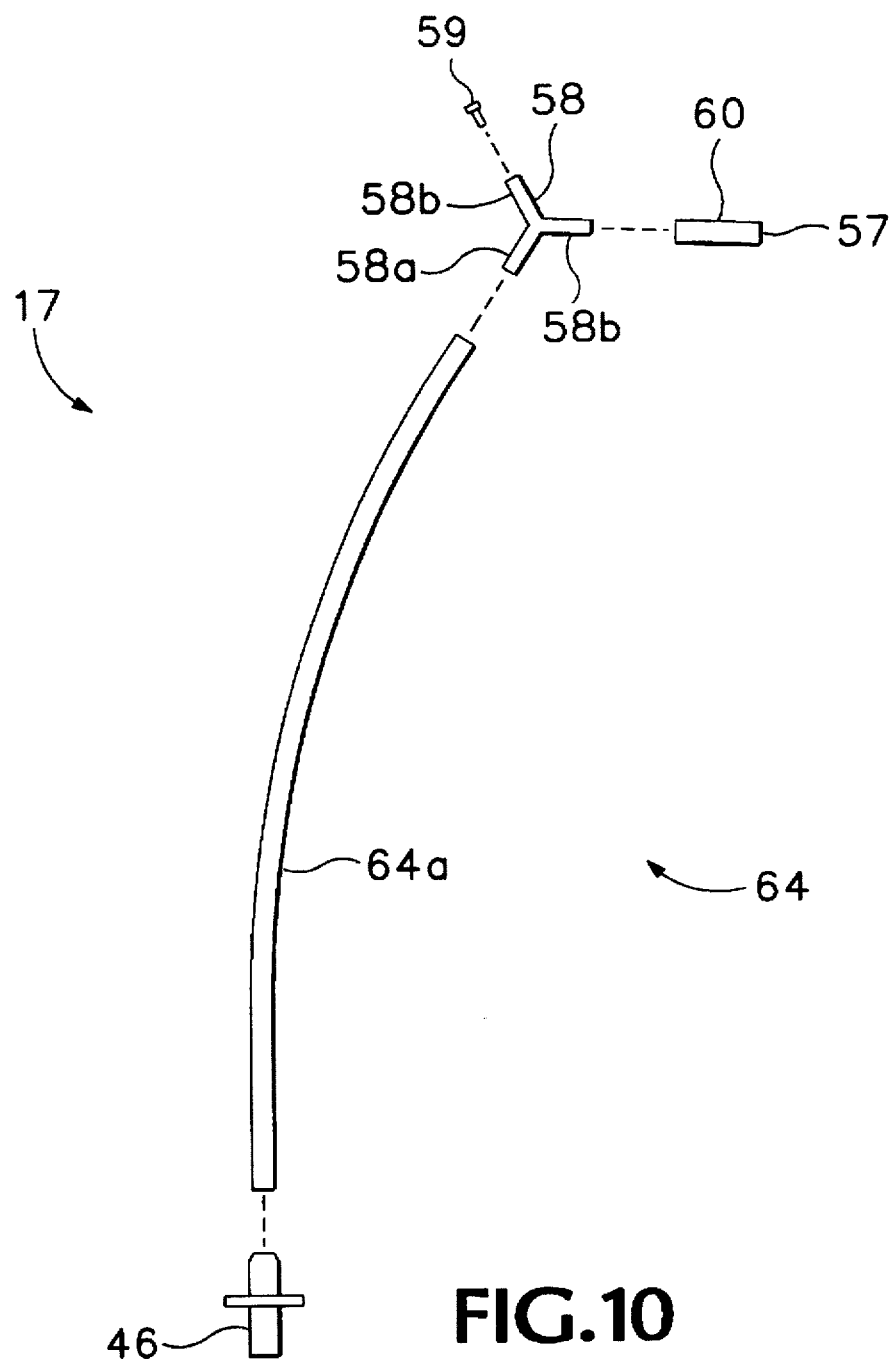
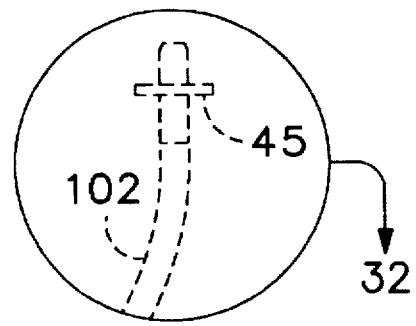
FIG.10

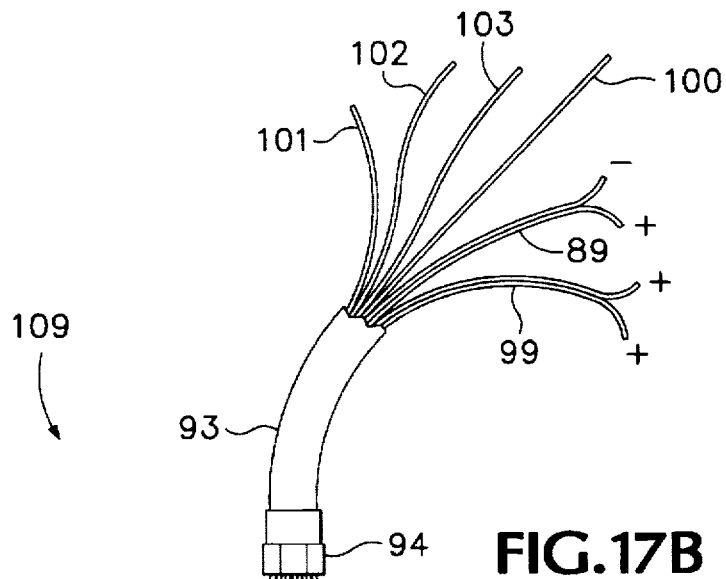
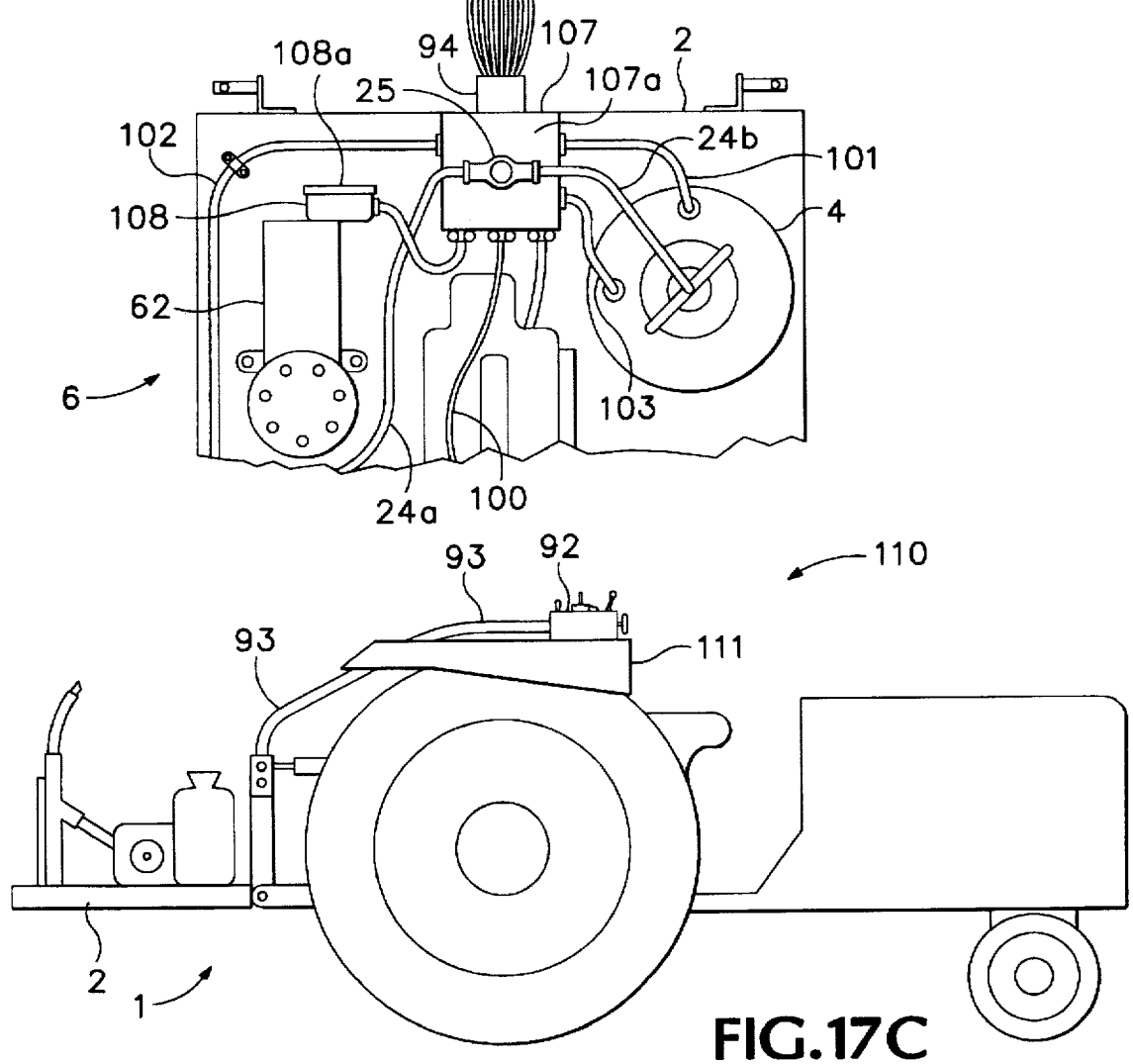

METHOD FOR FORMING AND APPLYING BIOLOGICAL CONTROL SYSTEM

RELATED APPLICATION

This application is related to patent application U.S. Ser. No. 08/423,765, filed by the U.S. Government for an invention entitled "Beneficial Insect Egg Spraying Device."

BACKGROUND OF THE INVENTION

Knowledge of the environmental impact of chemicals is increasing. At the same time, laws, regulations and registration regarding chemicals are proliferating and changing. Accordingly, since governmental regulation has increased, control of harmful pests and predators, such as insects, weeds, and animals, must be accomplished through the use of environmentally acceptable methods.

Biological control has proven successful in many instances for the control of harmful pests and predators. The success of such biological control depends, however, upon the use of (a) a control agent for a target harmful pest, (b) proper timing of application of the control agent, and (c) precise depositing of control agents in contact with the harmful pests and predators.

The enemies of biological control are many and varied. Insect eggs which are not deposited and placed properly in their natural environment are subject to being eaten by many other insects. The eggs can also hatch and be ineffective. Larva may be eaten by predators. Also, larva can die before reaching the plant target area. Predatory mites, insect eggs and bacterial agents all have special placement needs depending on the particular variety being protected and the control agent being used.

Some problems associated with previously used commercial and experimental bio-carriers include toxicity to the biological control agent, the inability to suspend a control agent properly to facilitate uniform distribution upon application, too much or not enough adhesive properties, lack of variability in the adjustability of either its suspension or adhesive qualities.

Therefore, a need exists for a bio-carrier that is non-toxic to the biological agent, can be mixed at different rates to facilitate the suspension of a variety of sizes and densities of biological agents, and is sprayable through specialized equipment for biological control or through normal spray equipment, if permitted by the target crop and agent of choice.

SUMMARY OF THE INVENTION

The present invention is directed to a bio-carrier which is non-toxic to most biological agents, will suspend various agents for increased uniformity of delivery, has adjustable adhesive properties which simulates nature, has variability in its adhesives and suspension qualities, it decreases control agent mortality, and it enhances overall effectiveness by allowing more live control agent to reach the target. It does so by depositing, adhering and maintaining the control agent in the active use zone of the target crop.

More specifically, a method for forming a biological control system for application to a target crop in an active use zone is set forth herein. The method is directed to the steps of first providing a bio-carrier system. The system includes at least one active biological control agent, a soluble cellulose-containing compound and water. The system is non-toxic with respect to the active biological control agent. The soluble cellulose-containing compound acts as a carrier for transporting the active biological control agent through the atmosphere. It does so while maintaining the biological control agent in an active state. It also delivers, deposits and adheres the biological control agent in the area of the target crop while maintaining the biological control agents in an active state.

The active biological control agents are employed to protect the target crop from attack by harmful pests and predators which would harm or destroy the target crop in the active use zone. For example, lacewings are common predators of many insect pests and several lacewing species are being commercially mass produced for pest control purposes. Major target pests are many species of aphids, onion thrips, arachnids such as various types of mites, two-spotted spiders, grape leafhoppers, silverleaf whiteflies, mealybugs, etc. However, it must be remembered that lacewings are expensive and presently there is a lack of application techniques for effectively and efficiently releasing lacewing larvae or eggs. Target crops include, for instance, field-grown crops and fruits, greenhouse-grown vegetables and ornamentals, landscape and interioscape ornamentals.

Then, the soluble cellulose compound, the biological control agent and water are combined to form the biological control system. Preferably, the bio-carrier system is sprayed into the active use zone while maintaining the biological control agent in an active state. As for the active biological control agents, they typically comprise an adult insect, insect larva or insect eggs. The active biological control agents can also comprise arachnids or fungal or bacterial agents.

The soluble cellulose-containing compound preferably is selected from a group consisting of carboxymethyl cellulose, hydroxyethyl cellulose, hydroxypropyl cellulose, hydroxy cellulose, and methyl cellulose. A preservative material can also be added for increasing the shelf life of the soluble cellulose-containing compound. The preservative material comprises methyl perecept or sodium benzoate.

When the method of the present invention is employed, the target crops can be grown above ground level, i.e., in trees, plants, bushes or the like. And, when the bio-carrier system is transported through the atmosphere, the soluble cellulose-containing compound prevents the active biological control agents from falling or being blown to the ground. Typically, the bio-carrier system is transported by spraying the bio-carrier above ground level and the biological control agents are maintained in an active state.

In a preferred method for forming a biological control system for application to a target crop in an active use zone, a concentrated bio-carrier system is employed to which water is added thereby forming the subject biological control system. The bio-carrier system is as described above except that the water portion is subsequently added to the concentrated mixture. This latter method generally includes the further step of diluting the bio-carrier system and then combining the diluted bio-carrier system with at least one active biological control agent. The biological control agent is then delivered, deposited and adhered in the area of the target crop while maintaining the biological control agents in an active state, the active biological control agents being employed to protect the target crop from attack by harmful pests and predators which would harm or destroy the target crop in the active use zone.

The foregoing and other objects, features and advantages of the invention will become more readily apparent from the following detailed description of a preferred embodiment of the invention.

BRIEF DESCRIPTION OF THE DRAWINGS

FIG. 10 is a perspective exploded view of aqueous solution system 17 for spraying trees with beneficial insects.

FIG. 12a is a perspective view of the mounting assembly 75 for air system 14 with aqueous solution system 16.

FIG. 12b is a perspective exploded view of slide bar assembly 79 that fits on either end of strut system channel 77 seen in FIG. 12a.

FIG. 17b is a top view of ESD 1 on deck and framework 2 showing electrical conduit 93 which connects wires and tubing of ESD 1 to remote control assembly 109 that sits on tractor fender 111.

FIG. 17c is a side view of ESD 1 on deck and framework 2 hitched to tractor 110 with remote control assembly 109 attached to fender 111.

DETAILED DESCRIPTION OF THE PREFERRED EMBODIMENTS

Figure 1:
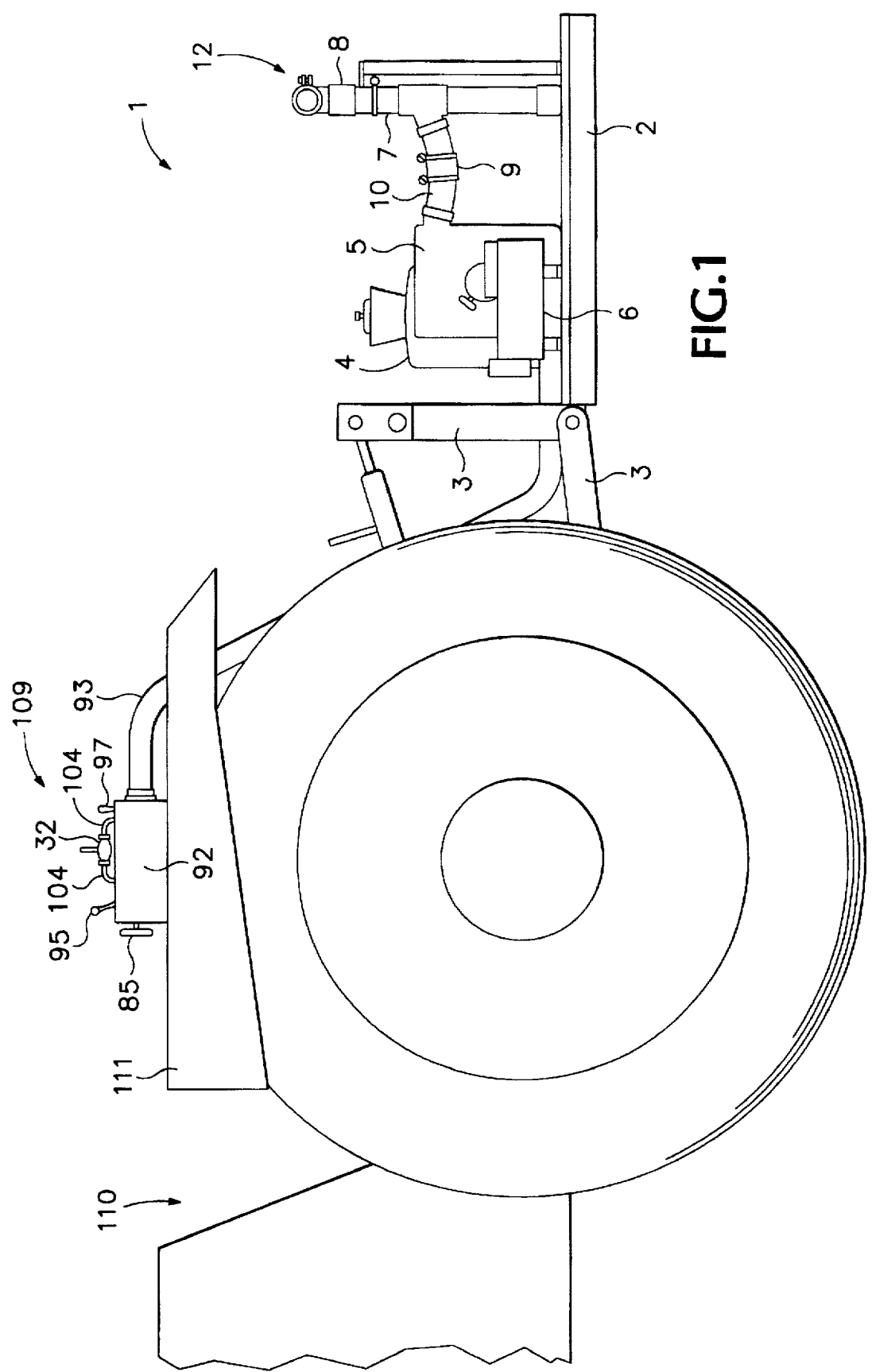
FIG. 1 is a side view of ESD 1 with air system 12 for spraying moderate height plants with beneficial insects.
Figure 2:
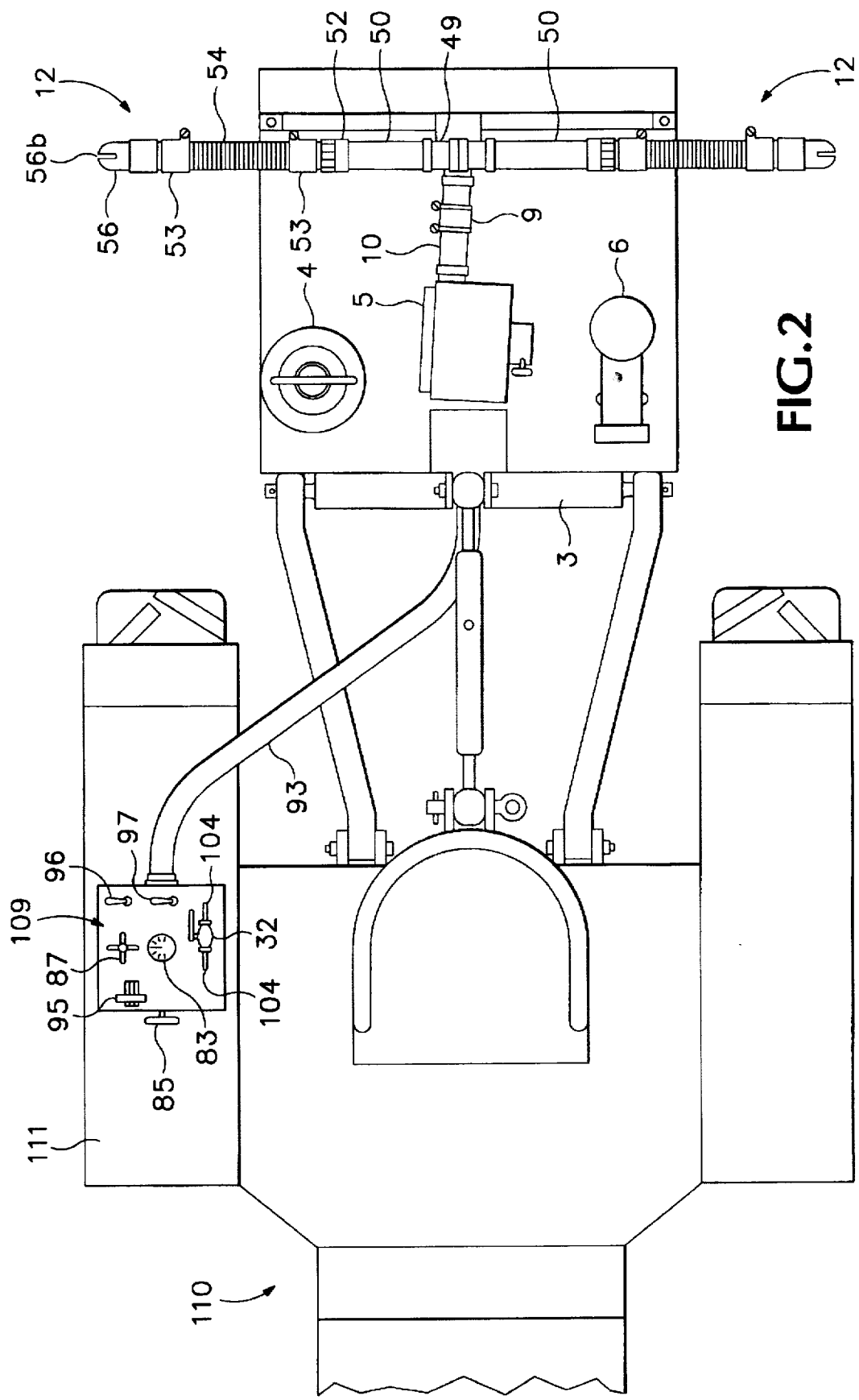
FIG. 2 is a top view of ESD 1 with air system 12 for spraying moderate height plants with beneficial insects.
Figure 3:
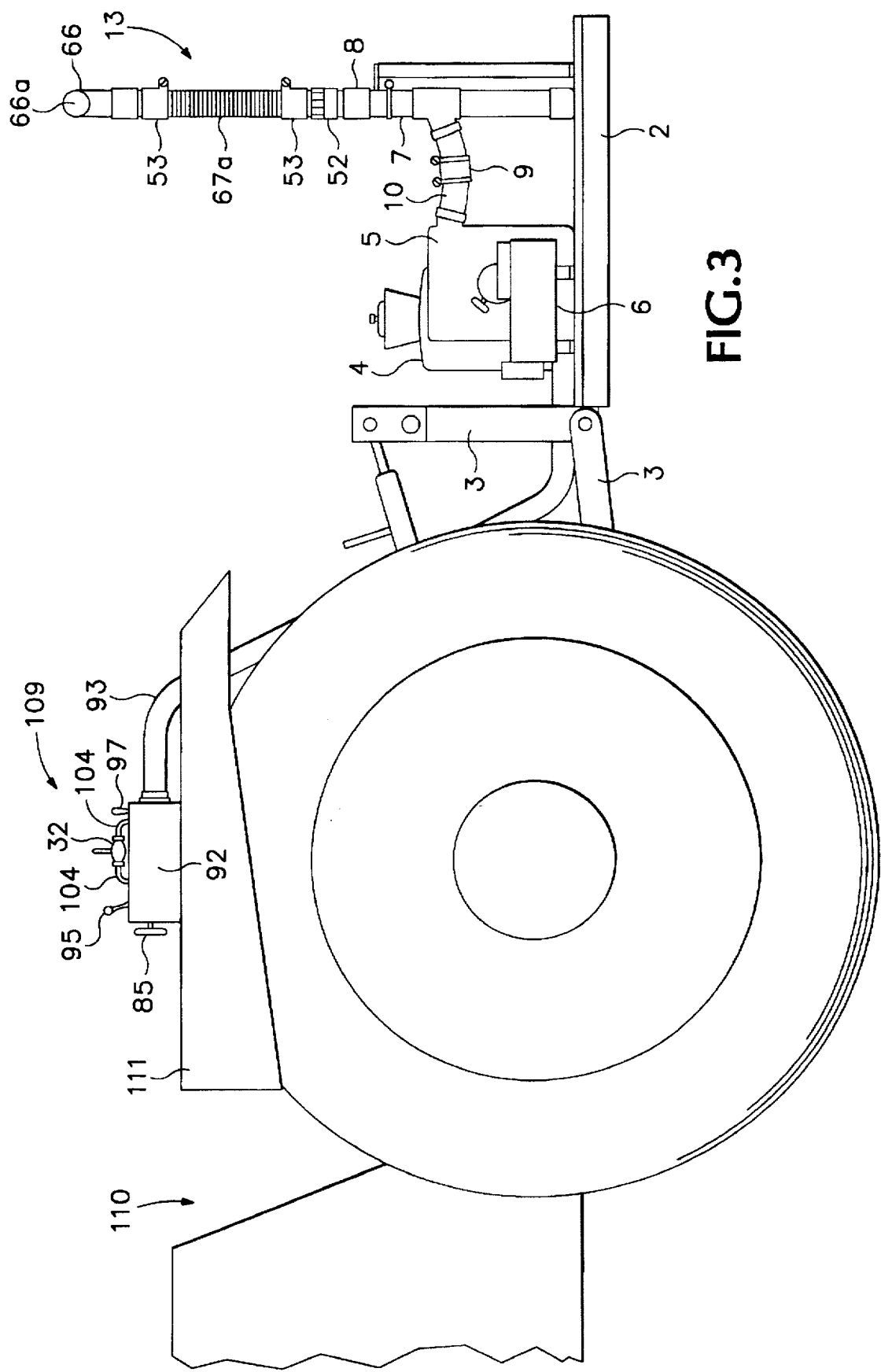
FIG. 3 is a side view of ESD 1 with air system 13 for spraying trees with beneficial insects.
Figure 4:
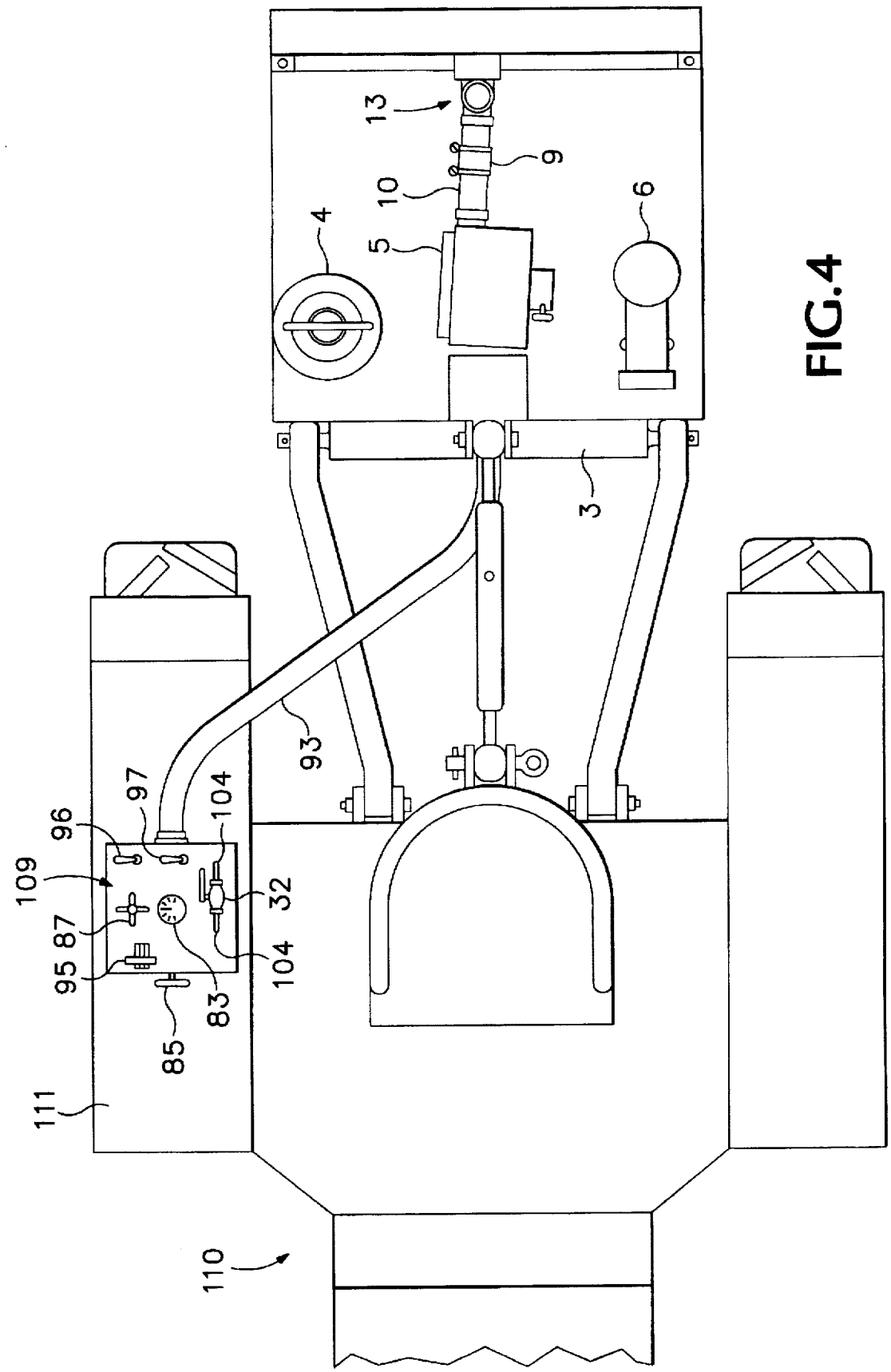
FIG. 4 is a top view of ESD 1 with air system 13 for spraying trees with beneficial insects.
Figure 5:
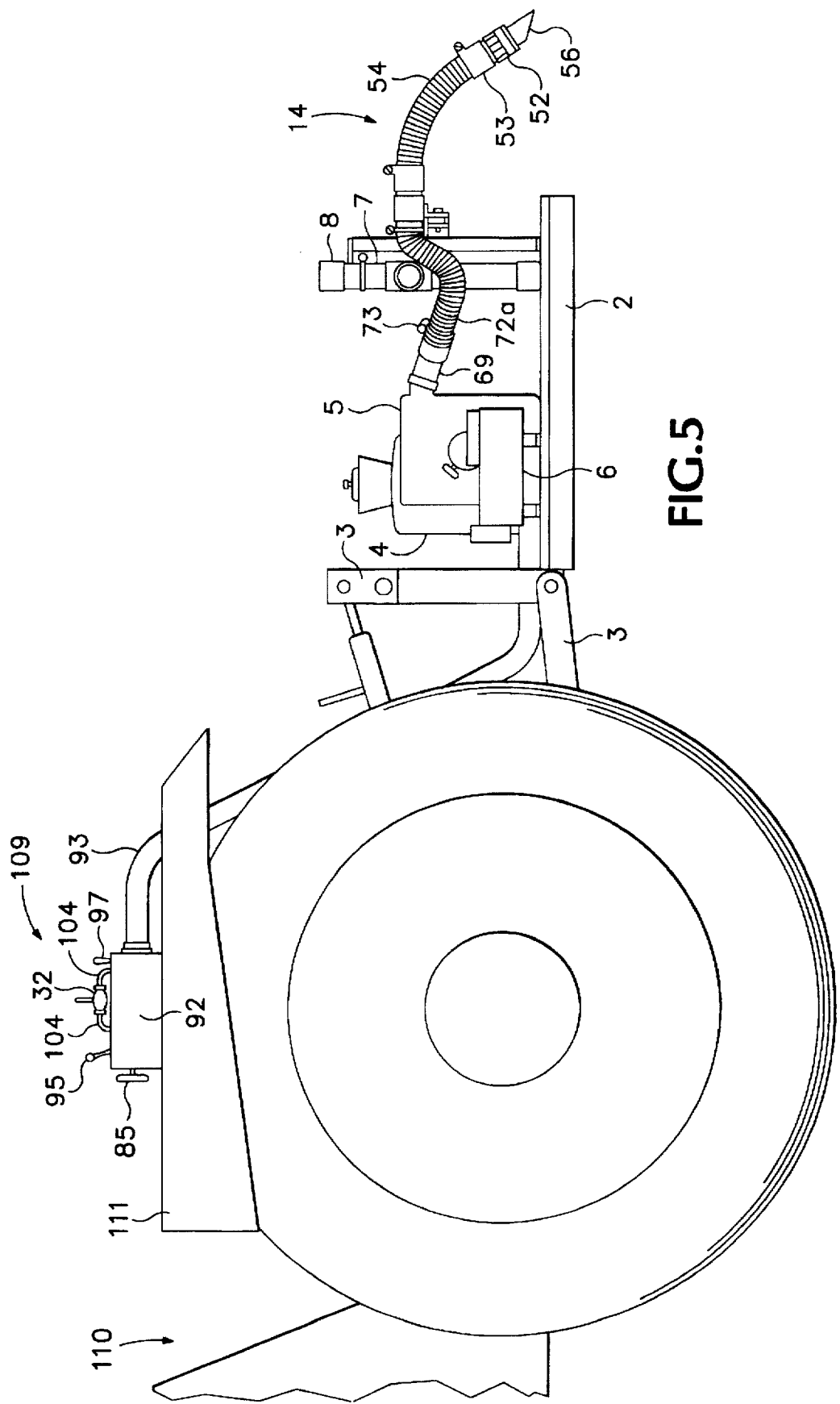
FIG. 5 is a side view of ESD 1 with air system 14 for spraying row crops with beneficial insects.
Figure 6:
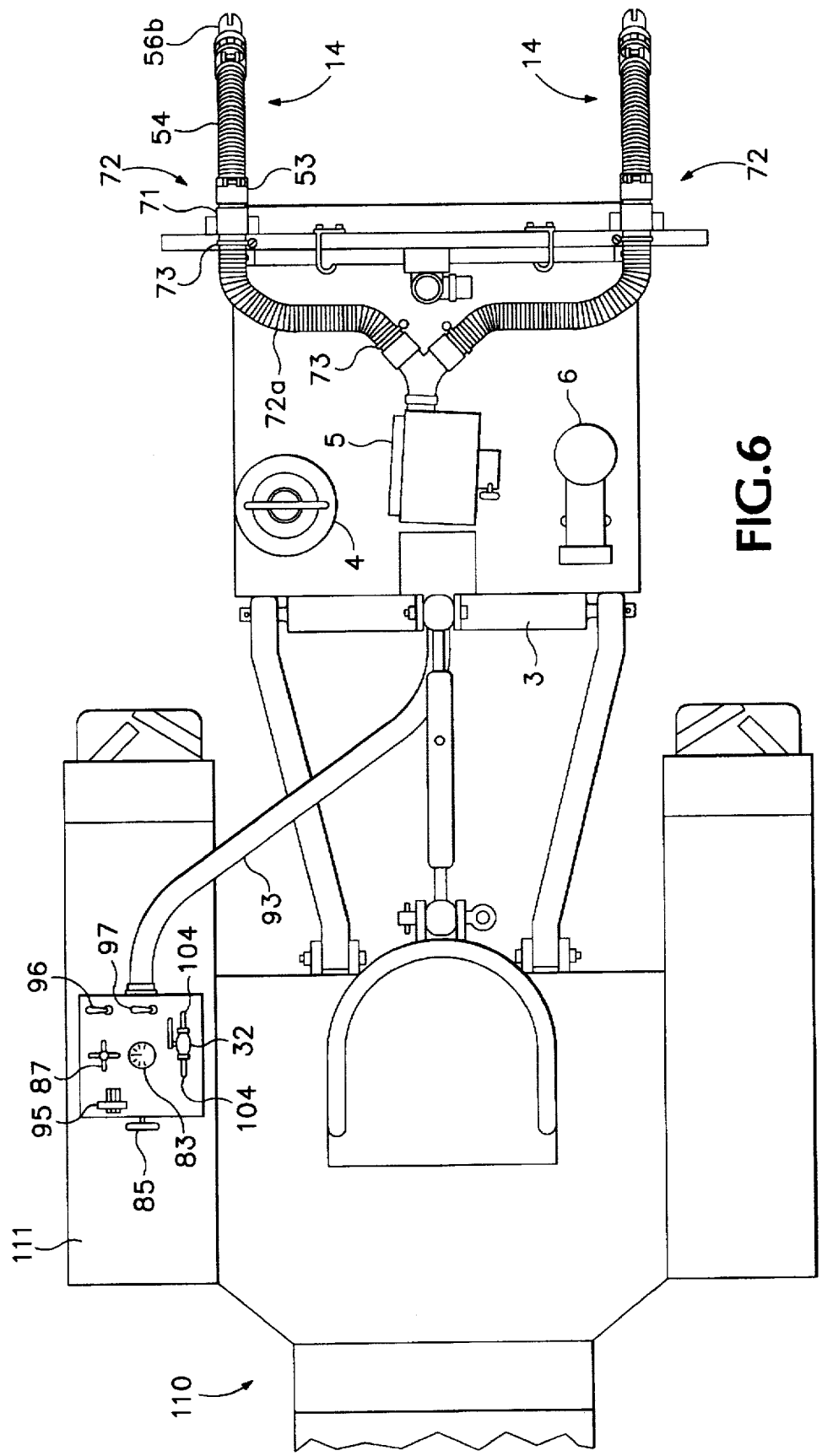
FIG. 6 is a top view of ESD 1 with air system 14 for spraying row crops with beneficial insects.

A preferred bio-carrier system was prepared by combining 50 grams of carboxymethyl cellulose with a gallon of water and 3.0 grams of methyl peracept preservative to form a bio-carrier concentrate. The concentrate was diluted 8:1 by volume with water and lacewing eggs were added to the holding tank of Specialty Sprayer System manufactured by Smucker Manufacturing Company of Harrisburg, Oreg., containing the preferred bio-carrier system described above. The bio-carrier including the lacewing eggs was sprayed onto plant leaves for pest control purposes. The sprayer action transported the bio-carrier and lacewing eggs to the plant leaves without damaging the eggs. The adhesive action of the bio-carrier caused the eggs to stick to the foliage without suffocating the eggs. Thereafter, the lacewing eggs hatched and the lacewings devoured pests such as aphids, whiteflies, leafhoppers, scales and mites that harm the plants. This technique eliminated the use of harmful chemical sprays and brought about the desired pest control through the use of biological treatment.

The preferred spray apparatus has been developed by the U.S. Government, is set forth in related patent application U.S. Ser. No. 08/423,765, entitled "Beneficial Insect Egg Spraying Device", which is incorporated herein by reference, and which is described as follows:

Beneficial insect egg spraying devices (ESDs) 1 incorporating the features of the present invention are illustrated in FIGS. 1–6. ESD 1 is made up of one of several air systems 12, 13, or 14 (FIGS. 7–11), a pressure release system 15, one of two aqueous solution assemblies 16 or 17, a compressed air system 18, a tank assembly 11, and a remote control assembly 10g. ESD 1 is mounted on a deck 2 supported by a tractor 3-point hitch 3 with part of the remote control assembly 109 mounted on tractor fender 111.

Figure 7:
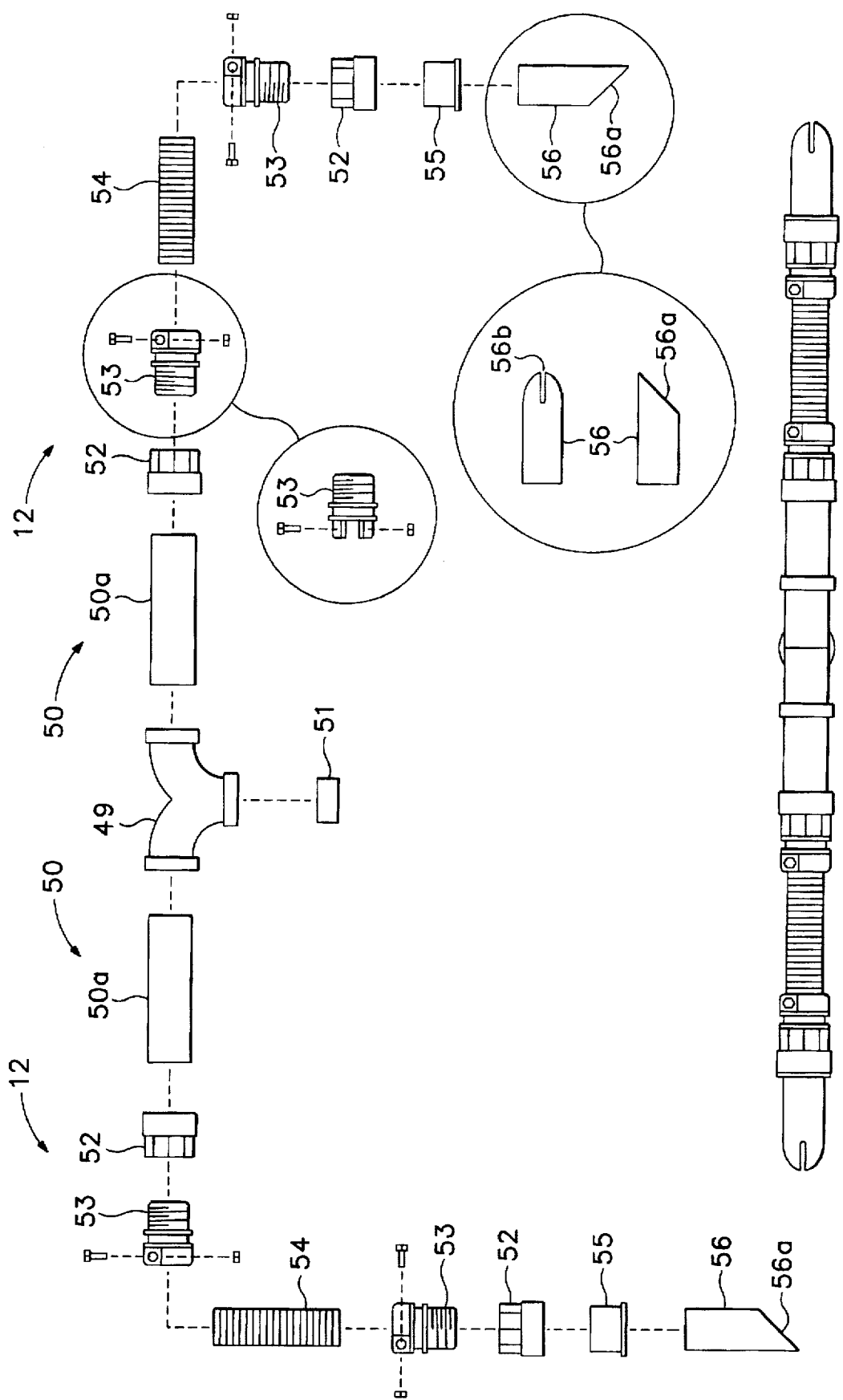
FIG. 7 is a perspective exploded view of air system 12 for spraying moderate height plants with beneficial insect eggs.
Figure 13A:
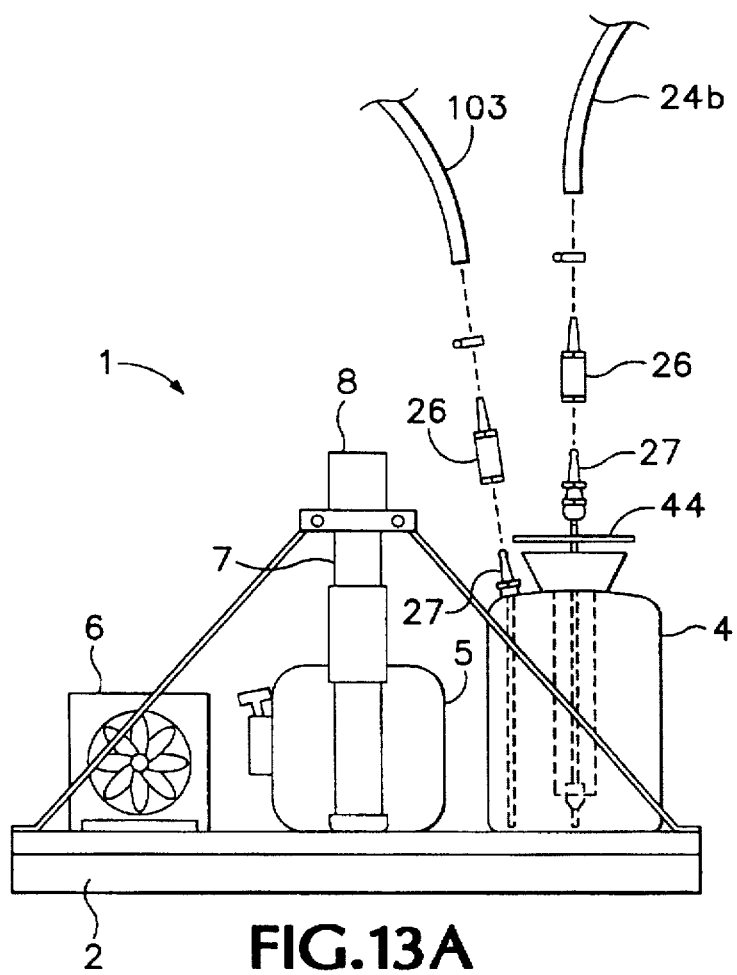
FIG. 13a is a perspective back view of ESD 1 mounted on deck and framework 2.
Figure 13B:
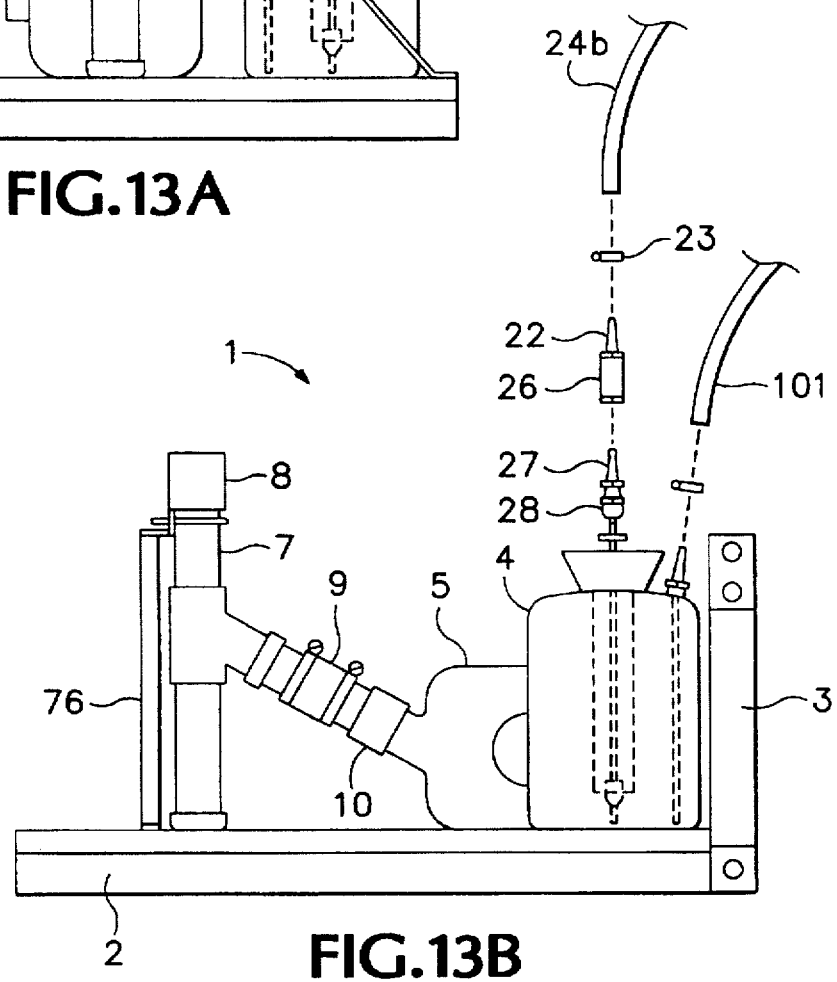
FIG. 13b is a perspective side view of ESD 1 mounted on deck and framework 2.

The first embodiment has an air system 12 useful for spraying beneficial insect eggs onto plants of moderate height such as grapes, hedge rows, shrubs, etc. The air system 12 has two spraying arms 50, 180 degrees apart, connected by a 2" PVC drain tee 49 (see FIG. 7). Tee 49, with a 2" length of 2" ID PVC pipe 51 connected at the inner end 49a of tee 49, connects air system 12 to gasoline engine driven blower fan 5 (Echo®, Echo, Inc, 400 Lakewood Road, Lake Zurich, IL 60047) (FIG. 13b) through a vertical 2" PVC s+and pipe 7 with a 2" receiving coupling 8 (FIGS. 13a and 13b). Each arm 50 is made up of a series of pipes and connectors either glued or threaded together. For each arm 50, glued to the outer end 49b of tee 49 is an 8" length of 2" ID PVC pipe 50a. Glue-fitted to the outer end of pipe 50a is a 2" ID PVC female adaptor 52. Threaded into the outer end of adaptor 52 is a 2" greenfield squeezetype flex/box connector 53. A 10¾" length of 2" flexible exhaust pipe 54 is connected to connector 53. On the outer end of pipe 54 is a second greenfield squeezetype flex/box connector 53. A second 2" PVC female adaptor 52 is threaded on to connector 53. Glue-fitted to the end of adaptor 52 is a 2"–1½" (reducer bushing 55. Glued to the 1½" end (outer end) of bushing 55 is a 3½" length of 1½" ID PVC pipe 56 with the outer end cut at a 45' angle to form air outlet port 56a. Pipe 56 has a ¼"×1⅛ ((longitudinal slot 56b cut into its top to receive aqueous solution outlet port 57 (FIG. 8) The total length of each spray arm 50 is approximately about 27¼" (FIG. 7).

Figure 16:
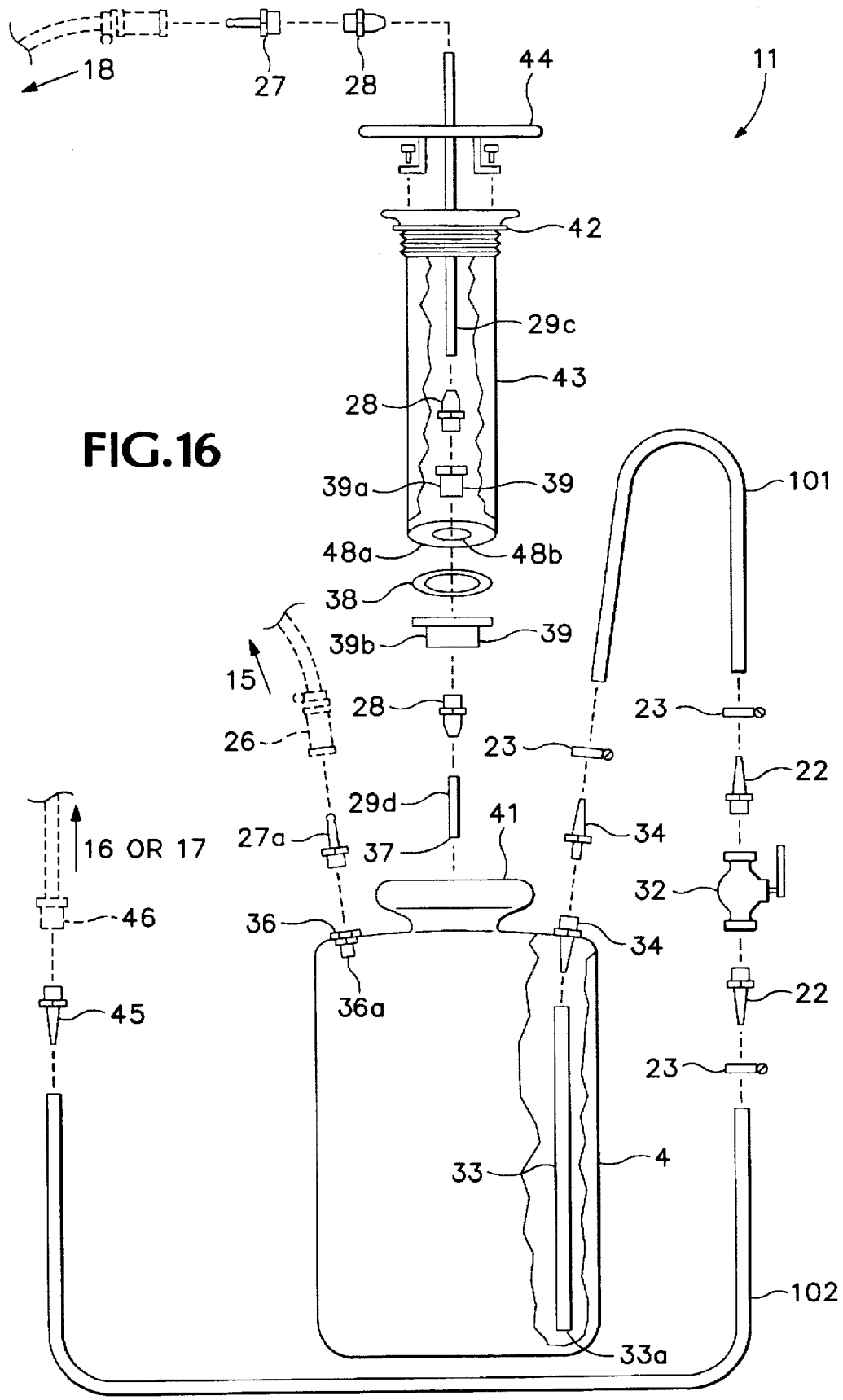
FIG. 16 is a perspective exploded view of tank assembly 11 showing the connections to compressed air system 18, pressure release system 15, and air systems 12, 13, or 14.

Aqueous solution assembly 16 is connected to spray arms 50 of air system 12 and to spray tank 4 through ¼" brass ball valve 32 (flow valve) (see FIGS. 8 and 16) of tank assembly 11. Assembly 16, like air system 12, has two arms 61, 180° apart, connected by an 8 mm plastic barbed Y-fitting 62. The inlet port 62a of fitting 62 is connected with a 2½" length of ⁵⁄₁₆ ID TYGON™ tubing 63, attached to, ¼" brass ball valve 32 through tubing 102 attached to a male ⁵⁄₁₆ plastic union 45 connected to a female ⁵⁄₁₆ plastic union 46. Tubing 63 attaches to the barbed end of female union 46. Each arm 61 is made up of tubing and a Y-fitting. A 30" length of ⅛" ID TYGON™ tubing 61a is attached to one of outlets 62b of Y-fitting 62 and to 6 mm plastic barbed Y-fitting 58 at inlet 58a. A one-inch length of ³⁄₃₂ ID TYGON™ tubing 60 is stretched over the end of one of the outlet ports 58b of fitting 58. The other port 58bis sealed with threaded plug 59 screwed into the port.

The second embodiment is air system 13 (FIG. 9), useful for spraying commodities such as pecan trees, walnut trees, Christmas trees, or anything that is a tree or grows on a tree.

The air system has a single spraying arm 67 which is attached to blower fan 5 through vertical 2" ID PVC stand pipe 7 with a 2" receiving coupling 8 (FIG. 13b). A 2" length of 2" ID PVC pipe 51 is inserted into coupling 8. A 2" PVC female adapter 52 attaches to the outer end of pipe 51 and a 2" greenfield squeeze-type flex/box connector 53 attaches to the outer end of adaptor 52. A 12" length of 2" ID flexible exhaust pipe 67a is attached to the outer end of connector 53 and a second greenfield squeeze-type flex/box connector 53 is attached to the outer end of pipe 67a. Second connector 53 is threaded onto a second 2" PVC female adaptor 52 which has a 5" length of 2" ID PVC pipe 66 glued to adaptor's 52 outer end. Pipe 66 is cut at a 45° angle to form air outlet port 66b. A ¼"×1⅝" longitudinal slot 66a is cut into the longest side of the top of pipe 66 Slot 66a receives tubing 60 of aqueous solution assembly 17 (FIG. 10).

Figure 9:
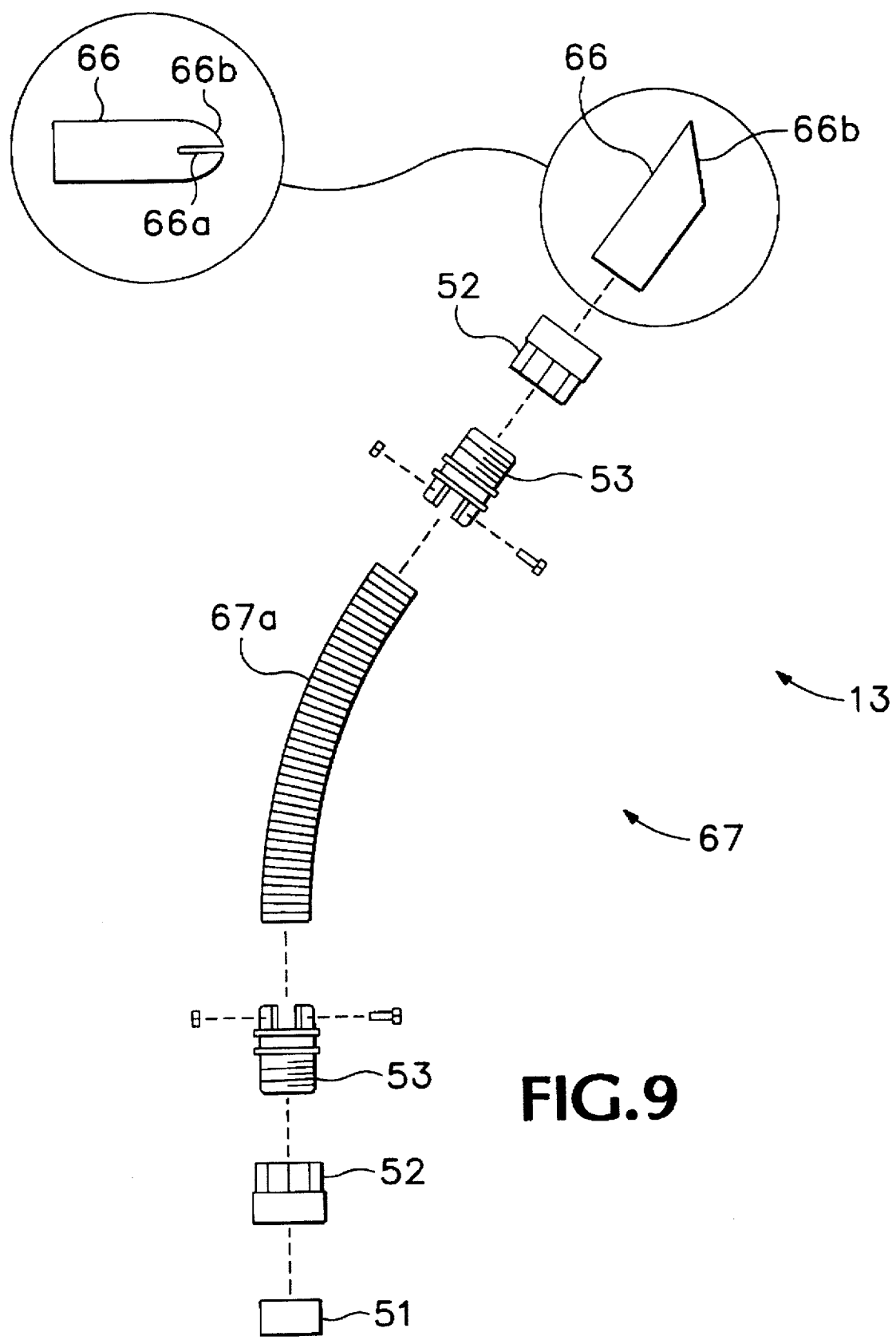
FIG. 9 is a perspective exploded view of air system 13 for spraying trees with beneficial insects.
Figure 11:
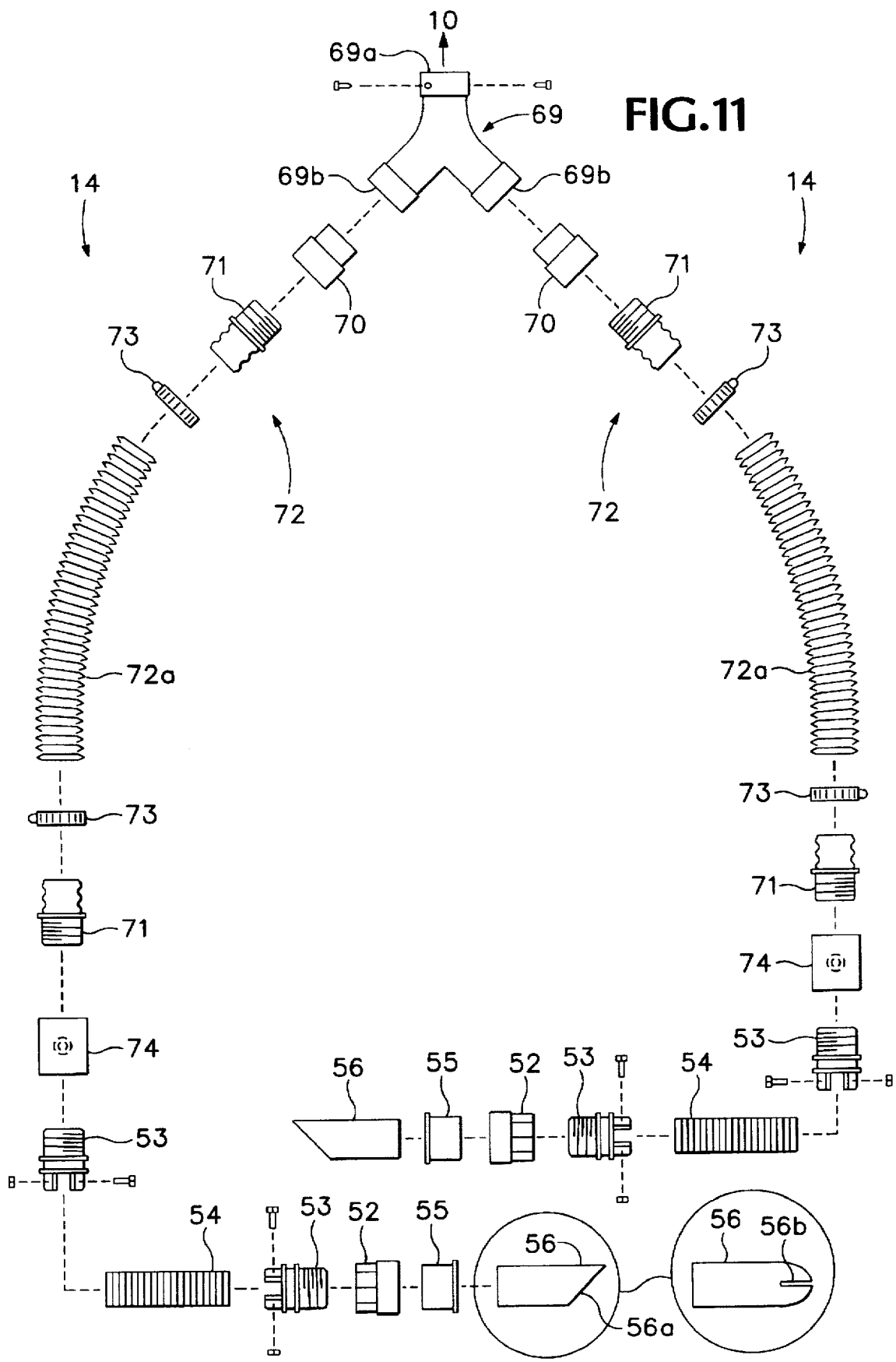
FIG. 11 is a perspective exploded view of air system 14 for spraying row crops with beneficial insects.

Aqueous solution assembly 17 is connected to spray arm 67 and to spray tank 4 through ¼" brass ball valve 32 of tank assembly 11 through 3/16 male plastic union 45 as described above for the first embodiment of the air system (FIG. 10). Assembly 17 is a single arm 64 connected to a 3/16 female plastic union 46. A 21" length of ⅛" ID TYGON™ tubing 64a attaches to the barbed end of union 46 and the outer end of tubing 64a attaches to a 6 mm plastic barbed Y-fitting 58 at inlet port 58a. As in the first embodiment, a 1" length of 3/32 ID TYGON™ tubing 60 is stretched over the end of one of outlet ports 58b of fitting 58. The other port 58b is sealed with threaded plug 59 screwed into the port. The outer end of tubing 60 forms aqueous solution outlet port 57. Tubing 60 inserts into the slot 66a of pipe 66 of air supply system 13 (FIG. 9).

Figure 12:
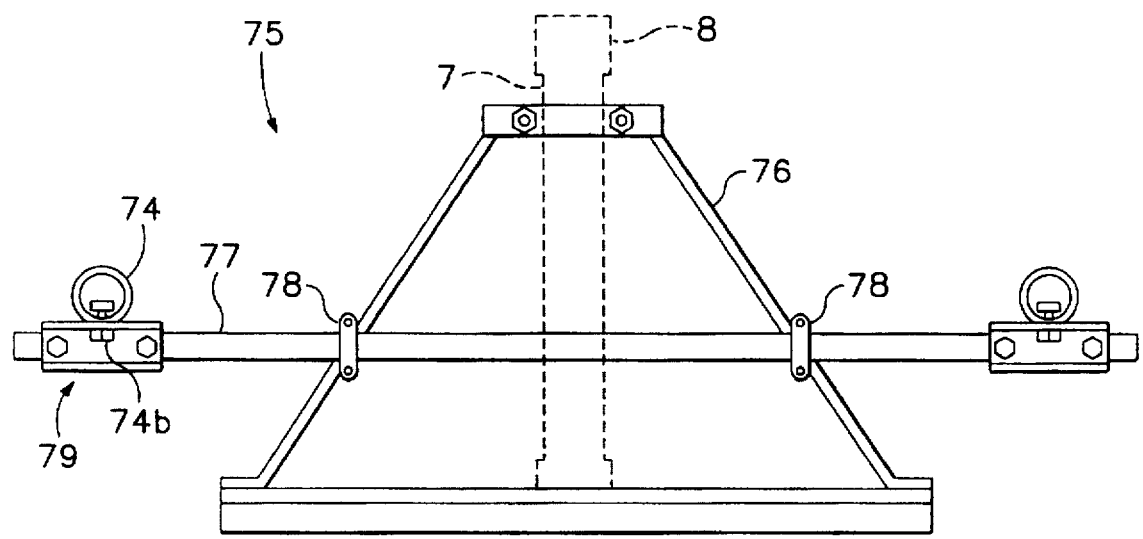
Figure 12B:
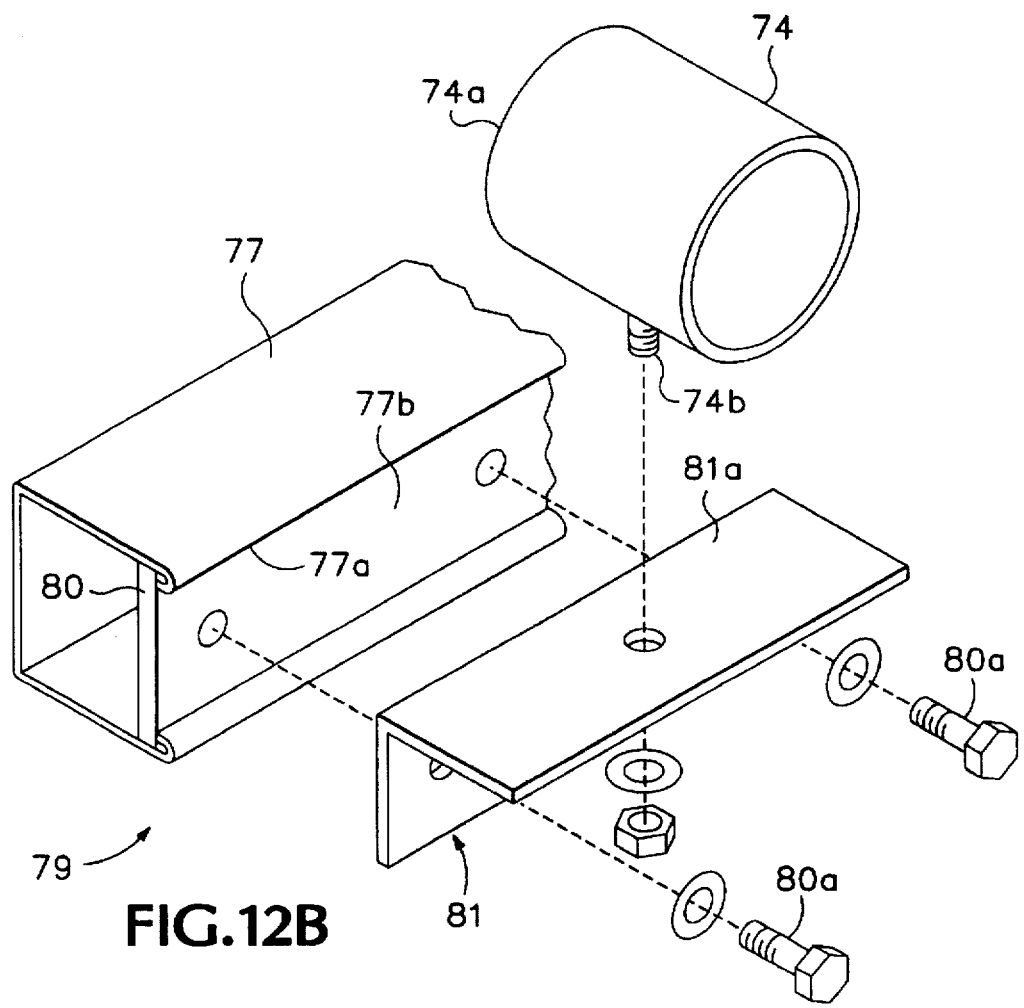

The third embodiment is air system 14 and, like system 12, has two spraying arms 72 (FIG. 11) useful for spraying row crops such as cotton, beans, peas, tomatoes, beets, lettuce, broccoli, strawberries etc. Air system 14 requires an alteration in the air supply assembly at the source of the air, blower fan 5 (see FIG. 13b). A 2" PVC coupling/blower connector 10, fastened to the housing of blower fan 5 by two sheet metal screws, is removed by loosening the hose clamps on rubber coupling 9, sliding the coupling towards blower fan 5, and rotating stand pipe 7 90° clockwise. Coupling/ connector 10 is removed and replaced with a 2" female PVC Y-fitting 69 where inlet end 69a is connected to blower fan 5 with the two sheet metal screws that held the 2" coupling/ blower connector 10 in place. For each spraying arm 72, a 2" PVC coupling female threaded/male glue joint 70 is fitted into each of the two outlet ports 69b of the Y-fitting 69. Threaded into coupling 70, is a 2" male plastic barbed fitting 71 upon which a 31" length of 2" ID flexible plastic hose 72a is attached with a medium size hose clamp 73. At the outlet end of flexible hose 72a, a second 2" male plastic barbed fitting 71 is attached with a second hose clamp 73. A modified 2" galvanized coupling 74 connects to threaded end of barbed fitting 71. Galvanized coupling 74 is modified by drilling a ¼" hole into the center of wall 74a, passing a ¼"×1½" carriage bolt 74b through the hole perpendicular to the direction of flow of air through the coupling (FIGS. 12a and 12b). Connected to the outlet end of modified coupling 74 is a 2" greenfield squeeze-type flex/box connector 53. A 10¾" length of 2" ID flexible exhaust pipe 54 is clamped to connector 53 and the outlet end of pipe 54 is clamped to a second 2" greenfield squeeze-type flex/box connector 53. Threaded onto connector 53 is a 2" female adaptor 52 in which a 2"–1½" reducer bushing 55 is glued. Inserted into reducer bushing 55 is a 1½"ID PVC pipe 56 cut at a 45 angle on one end to form air outlet port 56a.

The modified 2" galvanized couplings 74 are fastened to mounting assembly 75 (FIGS. 12a and 12b) with ¼" carriage bolts 74b. Assembly 75 includes about a 48" length of electrical strut system channel 77, two 3"×4" U-bolts 78, and a slide bar assembly 79. Channel 77 is held in place horizontally across the rear of the sprayer by two 3"×4" U-bolts 78 which are fastened to the stand pipe brace 76. Slide bar assembly 79 is made up of a 4" length of ¼" stock aluminum bar 80, 1¼" wide, which has been drilled and tapped to receive two 1"×⅜" machine bolts 80a and is inserted on the inside of the channel, resting on lips 77a of the open side 77b of channel 77 when bolted to a 2"×2"×¼" aluminum angle 81, approximately about 4" in length, on the outside of open side 77b of channel 77, forming a sliding and locking system which allows for adjustment to widths of rows. Coupling 74 is attached to the top 81a of angle 81.

The aqueous solution assembly 16 (FIG. 8) for air system 14 (FIG. 11) is the same assembly as that used with air system 12 as described above. Aqueous solution ports 57, inserted into slot 56b of angled pipe 56, and air outlet ports 56a, of angled pipe 56, are positioned onto mounting assembly 75 so that they face out from the rear of sprayer deck and framework 2 (not shown in FIGS. 12a and 12b). The delivered spray can be adjusted down onto the plants in the rows by bending the sections of 2" ID flexible exhaust pipe 54.

The tank assembly 11, pressure release system 15, compressed air system 18, and remote control assembly 109 are the same for each of the above air systems 12, 13, and 14 and aqueous solution systems 16 and 17.

Compressed air system 18 (FIG. 14) is made up of a 12 VDC Gast® diaphragm compressor 6 (1/16" HP, 50 PSI max. output) (Gast Manufacturing Corp., P.O. Box 97, Benton Harbor, Mich. 49023-0097), an air filter assembly 19 and a series of fittings and tubings which connects air filter assembly 19 and compressor 6 to spray tank assembly 11. A ¼" galvanized nipple 21, approximately about eight inches in length, is connected to air inlet 30 Of compressor 6. A ¼" galvanized elbow 82 is threaded onto the distal end of nipple 21 and is turned up so that air filter assembly 19 is positioned perpendicular to compressor 6 (normal mounting position). Connected to air outlet 31, of compressor 6, is a ¼" male brass barbed fitting 22 with approximately 26 inches of 3/16 ID TYGON™ tubing 24a fastened to the barbed end of fitting 22 and secured by small hose clamp 23. At the outlet end of tubing 24a is another ¼" male brass barbed fitting 22 and a small hose clamp 23. Fitting 22, attached to the outlet end of tubing 24a, is connected to a ¼" brass check valve 25 which blocks the passage of aqueous solution from spray tank 4 when the compressor is turned off while the tank remains under pressure. This protects the compressor's 6 diaphragm from the solution. Attached to the outlet end of check valve 25, is another ¼" male brass barbed fitting 22 which has approximately 28 inches of 3/16 ID TYGON™ tubing 24b fastened to fitting 22 outlet end with another small hose clamp 23. The outlet end of tubing 24b is fastened to another ¼" male brass barbed fitting 22 with a small hose clamp 23 This fitting 22 is connected at its outlet end to a quick disconnect female 26 (female threads which is mated with quick disconnect male 27 (female threads) which is an integral part of tank assembly 11 (FIG. 16) described below.

Figure 15:
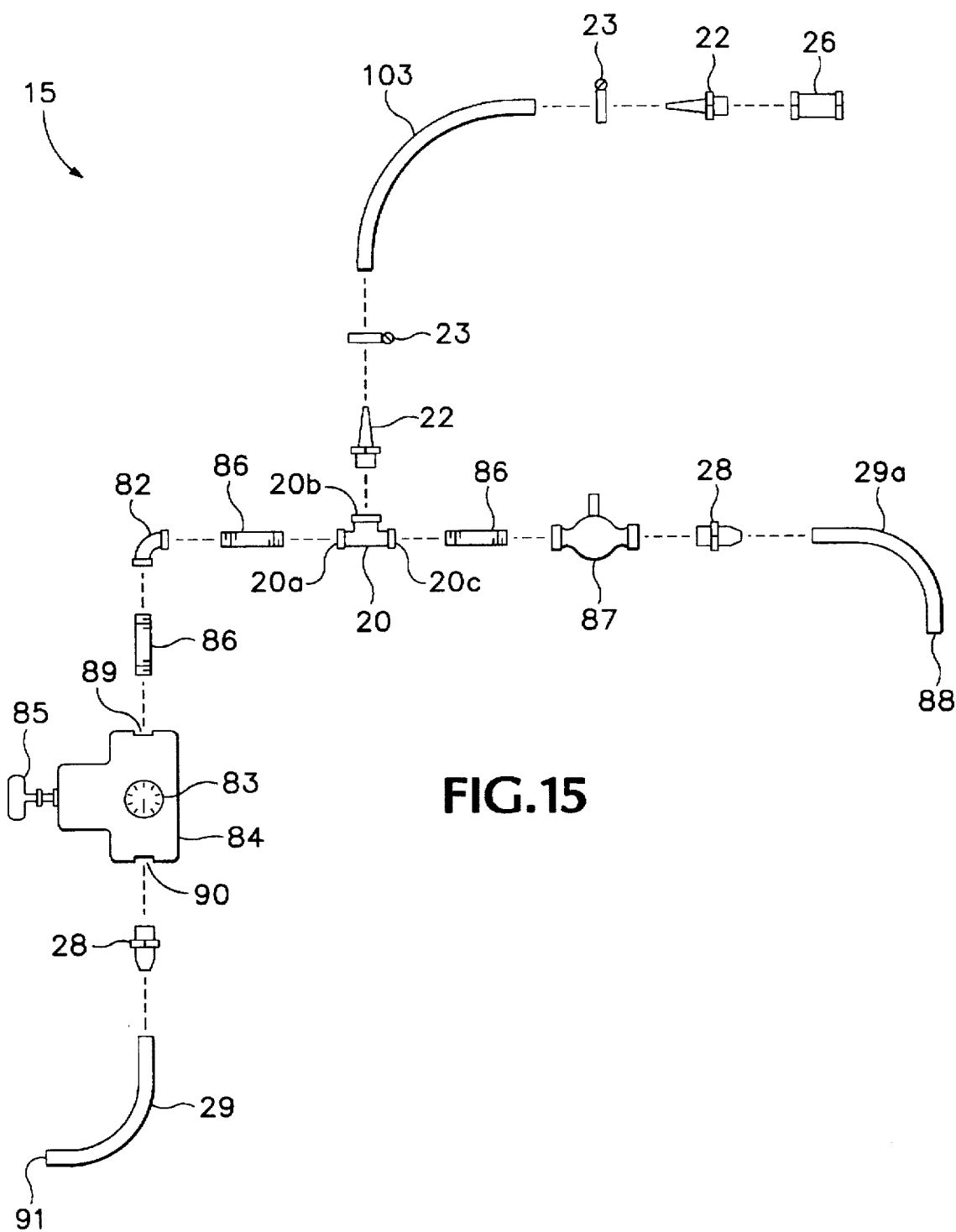
FIG. 15 is a perspective exploded view of pressure release system 15.

A bleed off system using a back-pressure regulator 84 that allows full throttle air into tank 4 for agitation while allowing the bleeding off of compressed air that is unnecessary to force the desired rate of aqueous solution out of the tank was designed in order to apply accurate rates of eggs onto target crops. Pressure release system 15 is shown in FIG. 15. A back pressure regulator 84 (0–60 PSI) (Bellofram Corporation, Newell, W.Va., 26050) is installed in the following manner: A ¼" galvanized nipple 86, approximately about 2½" in length, is threaded into inlet port 89 of regulator 84. A pressure gauge 83 (0–30 PSI) mounted on the regulator 84 serves as a reference point for back pressure settings when conducting multiple spray regimes on different crops or different rates of application. Control knob 85 is rotated clockwise to increase back pressure and counter clockwise to decrease back pressure. A ¼" galvanized elbow 82 is connected to the distal end of the first nipple 86. Another ¼" galvanized nipple 86 is threaded into the distal end of elbow 82. Threaded onto the distal end of the second nipple 86 is a ¼" galvanized tee 20 which serves as a point of junction for incoming compressed air bleeding off from tank 4 and the pressure release system 15. Inlet 20b of tee 20, located 90° from outlets 20a and 20c, is connected to a ¼" male brass barbed fitting 22. On the distal end of fitting 22 is approximately about 110 inches of 3/16 ID TYGON™ tubing 103 held in place by a small hose clamp 23. Inserted into the distal end of tubing 103, which is located on ESD 1, is another ¼" male brass barbed fitting 22, with tubing 103 held in place by another small hose clamp 23. A quick disconnect female 26 (female threads) is threaded onto the distal end of the second ¼" fitting 22. The quick disconnect female 26 is mated with a quick disconnect male 27a on tank 4 which places tank 4 in communication with the pressure release system 15. Connected to outlet 20c, of tee 20, is a ¼" ID galvanized nipple 86 which connects on its distal end to a ¼" pressure release needle valve 87. This valve serves as the means for depressurizing the whole system which is necessary before opening the fill port 47 of tank 4. This valve also allows back pressure regulator 84 to be set at a predetermined pressure setting which remains at the same setting after refilling tank 4. Connected to outlet side of valve 87 is a ¼" male ferrel adapter 28 which has approximately about 6 inches in length of ¼" OD copper tubing 29a attached to its distal end. Tubing 29a forms pressure release compressed air outlet port 88 at its distal end.

Connected to outlet port 90 of regulator 84 is a ¼" male ferrel adaptor 28 with approximately about 4 inches of ¼" OD copper tubing 29b. Tubing 29b forms compressed air bleed off port 91.

Figure 14:
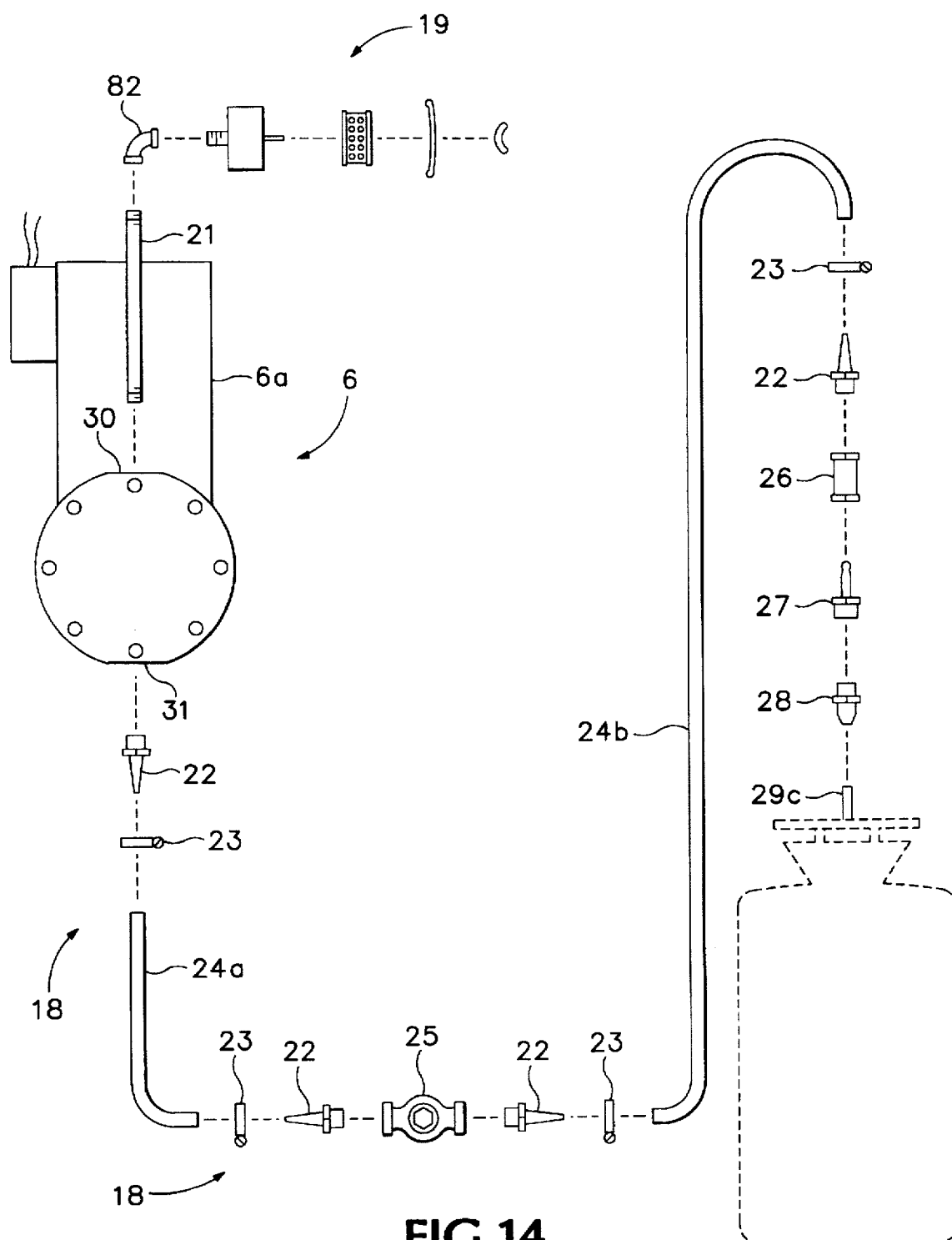
FIG. 14 is a perspective exploded view of compressed air system 18 showing its connection to spray tank 4.

Tank assembly 11 (FIG. 16) is made up of three ports that allow pressurization and agitation—port 37, flow of aqueous solution—port 33a, and pressure bleed off for control of flow of aqueous solution—port 36a. Spray tank 4 is a commercially available 2 gallon hand pressurized spray tank (RL Flo-Master Funnel Top Sprayer, RL Corp., Lowell, Mich. 49331) modified by removing the original hand pump assembly (not shown) from pump housing 43. Housing 43, which serves as the closing and seal of tank fill port 47, is modified in the following manner: A 1" diameter hole 48b is drilled in the bottom 48a of housing 43 (where the rubber check valve for the conventional hand pump was located) and ¼" plastic bung hole fitting 39 is inserted through hole 48b. The top 39a (male) of fitting 39 is inserted from inside housing 43 through hole 48b, extending outside housing 43, through rubber gasket 38 on the exterior bottom (8a of pump housing 43. Top 39a of fitting 39 then threads into the bottom 39b (female) of fitting 43. Threaded into top 39a of fitting 39 is a ¼" male ferrel adaptor 28 with approximately about 11¾ inches of ¼" OD copper tubing 29C attached to the outlet end. Tubing 29c extends upward through the hollow interior of pump housing handle 44, and extends approximately about 2" above the top of handle 44. A second ¼" male ferrel adapter 28 is connected to the exterior end of tubing 29c. A quick disconnect male (female threads) 27 is fastened to the inlet end of fitting 28. Disconnect 27 is mated to quick disconnect female 26 Of compressed air system 18 (FIG. 14). Attached to outlet end of bottom 39b of fitting 39 is a ¼" male ferrel adapter 28 which has a ¼" OD copper tubing 29d, approximately about 1¼ inches in length, attached to the outlet end of adapter 28. Tubing 29d places compressed air outlet port 37 approximately about 3/16 from the inside bottom of spray tank 4 when pump housing 43 is inserted into tank fill port 47 and tightened until rubber seal 42 mates with molded depression (not shown) in fill port 47.

Figure 8:
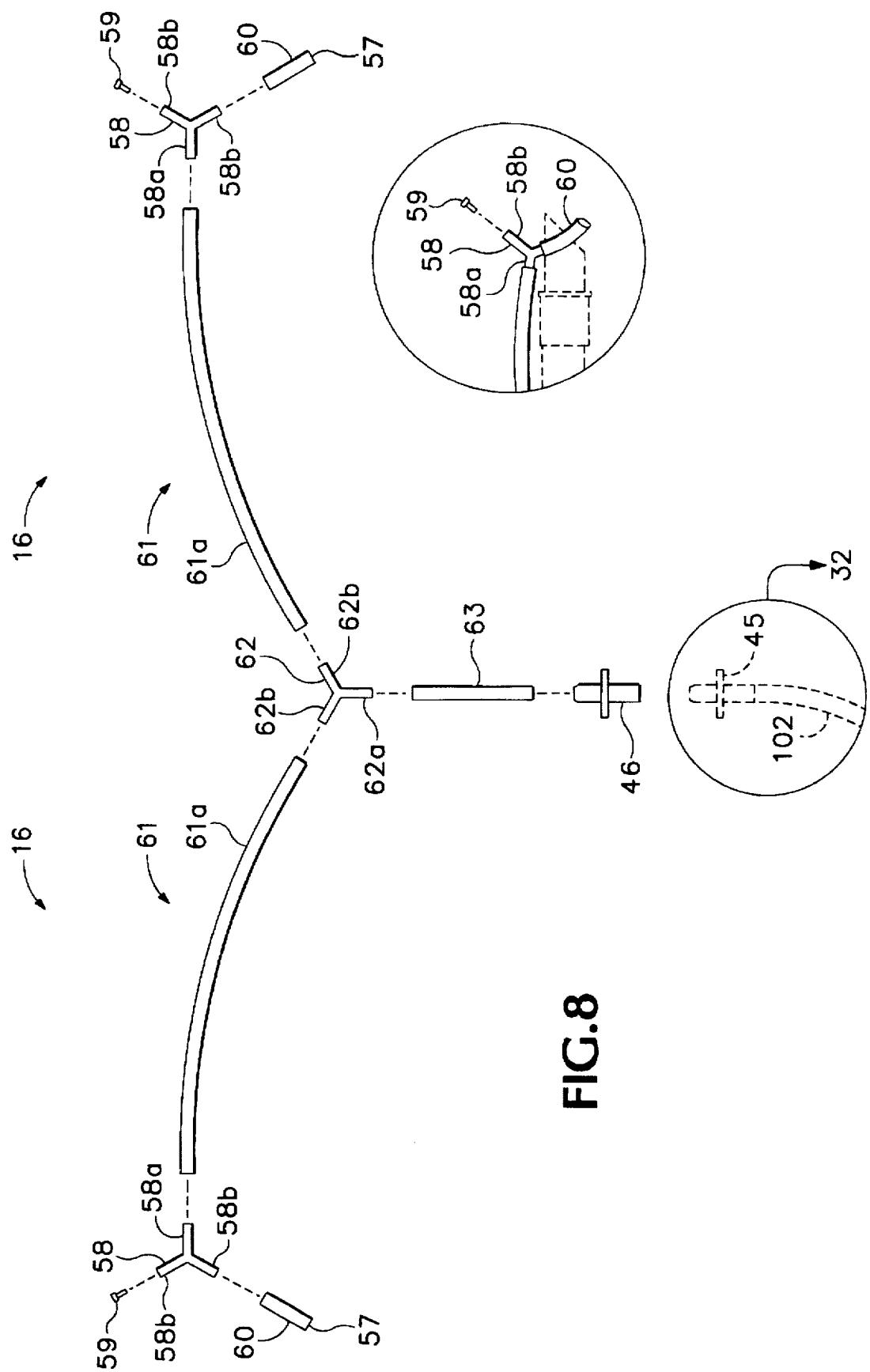
FIG. 8 is a perspective exploded view of aqueous solution system 16 for spraying moderate height plants and row crops with beneficial insects.

A ¼" plastic pick-up tube 33 and plastic adapter 34 are original parts of the hand sprayer and formerly served as the connection point of the original hose and wand. Aqueous solution inlet port 33a is formed by the inlet end of tube 33 which is attached to the inlet end of adapter 34. Attached to the barbed end of adapter 34 is 3/16" ID TYGON™ tubing 101, approximately about 110 inches in length, held in place by small hose clamp 23. The outlet end of tubing 101 is clamped by another small hose clamp 23 onto the barbed end of a ¼" male brass barbed fitting 22. The outlet end of fitting 22 is threaded into the inlet end of a ¼" brass ball valve 32 which serves as a flow control valve for the operation of the sprayer. Connected to the outlet end of valve 32 is another ¼" male brass barbed fitting 22. Attached to the outlet end of fitting 22 is a piece of 3/16" ID TYGON™ tubing 102, approximately about 146 inches in length, held into place by a small hose clamp 23, Tubing 102 is routed to the base of stand pipe 7 (FIG. 13a–13b) where a 3/16" plastic union 45 (male) is attached. Union 45 is mated to a 3/16" plastic union 46 (female) on aqueous solution system 16 or 17 (FIGS. 8 and 10).

Spray tank 4 is modified by drilling a ⅜" hole in the top shoulder of tank 4. A ¼" bulkhead fitting 36 is mounted in the hole and a quick disconnect male 27a (male threads) is attached to the outlet end of fitting 36. Quick disconnect 27a is mated with female quick disconnect 26 which is part of pressure release system 15, placing spray tank 4 in communication with pressure release system 15.

Figure 17A:
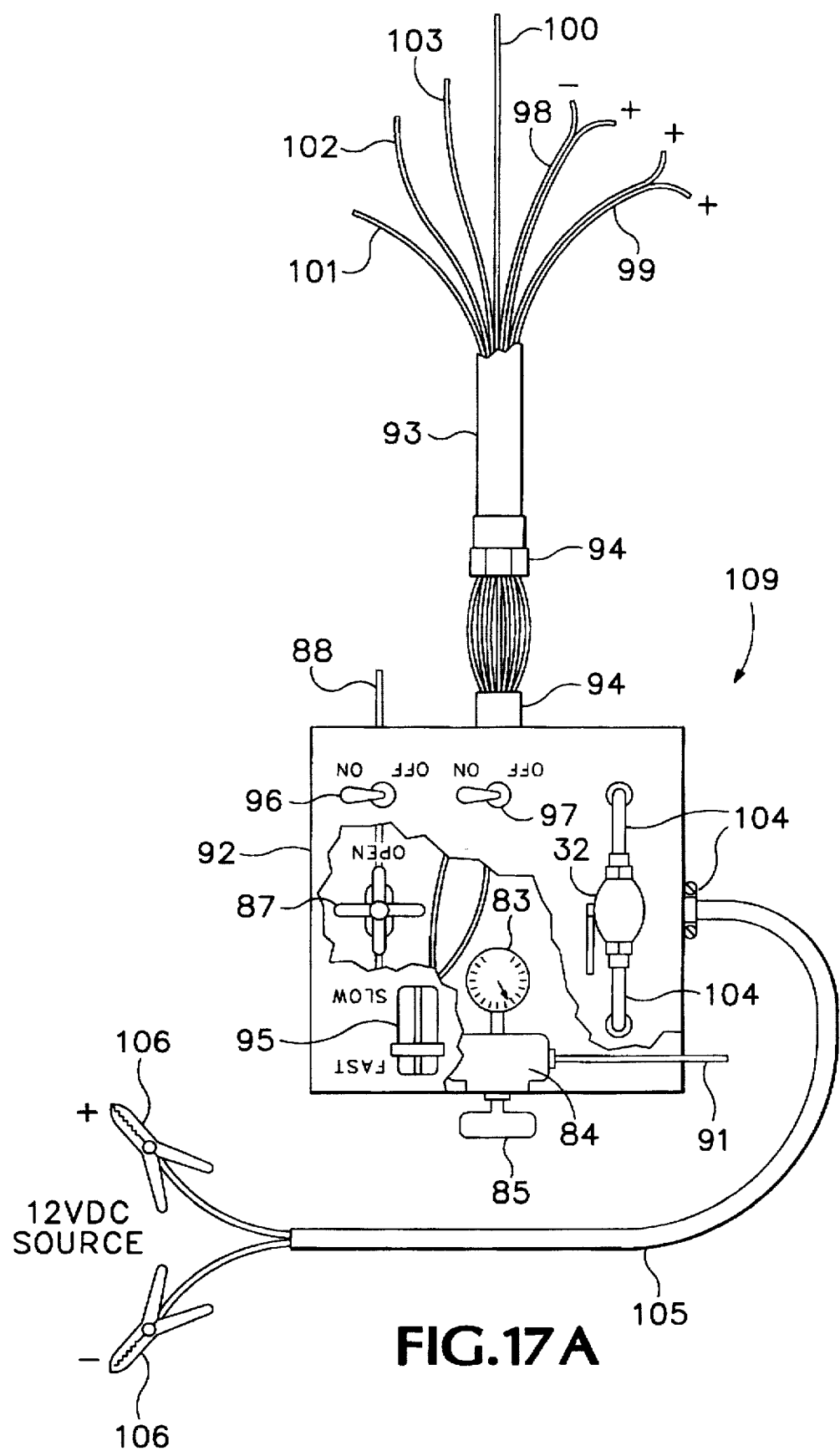
FIG. 17a is a view of remote control assembly 109.

Remote control assembly 109 (FIGS. 17a, 17b, and 17c) is made up of (1) pressure release system 15, (2) ¼" brass valve 32 (the flow control), (3) heavy duty 12 VDC automotive toggle switch 96 (for 12 VDC compressor), (4) a light duty kill switch 97 (for gasoline engine driven blower fan), and (5) a remote throttle control 95 for the gasoline driven blower fan 5. All of 15, 32, 95, 96, and 97 are mounted on or contained in control panel box 92 which is approximately about 10"×10"33 4". A 2" flexible covered electrical conduit 93 is attached to the remote control panel box 92 with a 2" flex/box connector 94. Remote control panel box 92 also receives a heavily insulated 12-2 electrical cable 105 with positive (+) and negative (−) alligator clips 106 which connect to the 12 VDC power source of a tractor, all-terrain vehicle (ATV) or any other vehicle suitable for spraying agricultural commodities. The positive lead (not shown) of cable 105 is connected to the heavy duty automotive toggle switch 96 through a 10 amp fuse link (not shown) in electrical junction box 108. With remote control panel box 92 mounted on the fender 111 of tractor 110 (right or left side, FIGS. 1–6, and 17c), the 2" flexible covered electrical conduit 93 is routed to the rear of tractor 110 and is attached to 6"×6"×3" electrical junction box 107 with a 2" ID flex/box connector 94. The 6"×6"×3" electrical junction box mounted on the front center of deck and framework 2 serves as a distribution point for all that is routed through conduit 93. The following components are routed through conduit 93 and link up remote control 109 with ESD 1: (1) a 110" length of 3/16 ID TYGON™ tubing which is aqueous solution tubing 101 from spray tank 4 to ¼" brass ball valve 32; (2) a 146" length of 3/16 ID TYGON™ tubing which is the aqueous solution return tubing 102 from brass ball valve 32; (3) a 110" length of 3/16 ID TYGON™ tubing which is compressed air bleed off tubing 103 from spray tank 4 to pressure release system 15; (4) a throttle control cable 100 which connects throttle 95 to blower fan 5 engine; (5) two 12 gauge automotive electrical wires 98 from power source and heavy duty electrical toggle switch 96 to compressor 6; and (6) two 18 gauge automotive electrical wires 99 from light duty kill switch 97 to gasoline engine driven blower fan 5. Visual flow tubes 104 are the outlet end of tubing 101 and the inlet end of tubing 102 which are attached to the inlet and outlet ends of valve 32, respectively. Tubes 104 enable an operator to visually observe the flow of eggs through the tubing in case of a stopped up tube or other malfunction. From the distribution point, junction box 107 and cover 107a, each component is routed to the appropriate connection point as described above for each system. The only system that does not pass through the remote control assembly 109 is the compressed air system 18 which is routed directly from compressor 6 to spray tank 4 with ¼" brass check valve 25 mounted on cover 107a of junction box 107. Electrical wires 98 are routed from the distribution point of junction box 107 to a 4"×2"×2" electrical junction box 108 with cover 108a which is mounted onto motor housing 6a of compressor 6 The positive (+) leads of wires 98 pass through a 10 amp fuse link (not shown) before connecting up with the positive (+) lead of compressor 6. The fuse link serves as protection for the compressor against a power surge or a mistaken connection to a power source greater than 12 VDC.

In the spray apparatus described above, the aqueous solution contains beneficial insect eggs, an adhering agent which will not adversely effect the beneficial insect eggs, and water. The concentration of the adhering agent in water is from about 2% to about 25% for good to excellent adhesive properties, with a more preferred concentration of from about 2% to about 15% for achieving a high percentage of eggs hatching. The adhering agent is a sprayable adhesive agent which is not toxic to the insect eggs and does not foul the sprayer. Examples of sticking agents which the inventors of the spraying apparatus have found to be useful, in addition to those described above, are a starch-sucrose formulation, or a flour-sucrose formulation, both as disclosed in U.S. Pat. No. 5,061,697. The beneficial insect eggs are used at a concentration of at least about 1,000 eggs per gallon. A limitation of the upper concentration range is the amount of eggs which will clog aqueous spraying system 16 or 17.

In operation, tractor 110 is driven between rows of agricultural commodities such as trees, grapes, tomatoes, etc. as the aqueous solution containing beneficial insect eggs in tank 4 is being pumped into tubings 101 and 102, controlled by ¼" brass ball valve 32 via inlet port 35, and tubing 63 on into spraying arms 61 of aqueous solution systems 16 (Embodiments I and II) or 17 (Embodiment III) via male and female unions 45 and 46 on tubings 63 and 64a, respectively. The eggs and aqueous solution exit the aqueous solution arms 61 through ports 57 and are blown onto the plants by air forced through ports 56a or 66b of spraying arms 50, 67, or 72 of the three different air systems 12, 13, or 14. Throttle 95 controls the flow of air from blower fan 5 to the arms of the different air systems 12,13, or 14. In addition, pressurized air, from compressor 6, is pumped into tank 4 to pressurize the tank and to provide continuous agitation of the aqueous solution in order to keep the eggs in suspension whether tank 4 is filled or near empty.

Furthermore, back pressure regulator 84 allows a full throttle of air from compressor 6 into tank 4 for agitation while allowing bleeding off of compressed air from tank 4, through bleed off port 91, to force the desired rate of flow of aqueous solution out of tank 4 through aqueous solution inlet port 33a. Regulator 84 also allows for different rates of applications and pressure gauge 83 serves as a reference point for back pressure settings when conducting multiple spray regimes on different crops. Compressor 6 with blower fan 5 provides the air, through stand pipe 7 (air systems 12 or 13) or through Y-fitting 69 connected directly to blower fan 5 (air system 14), that flows through spraying arms 50, 67, or 72 of air systems 12, 13, or 14 and propels the aqueous solution with eggs, exiting from port 57, away from ESD 1 and onto the agricultural commodities. To shut down the system, compressor 6 is shut off by toggle switch 96 and the gasoline engine of blower 5 is shut off by kill switch 97 on remote control panel box 92. When compressor 6 is turned off, the pressure release valve 87 of pressure release system 15 is opened to relieve tank pressure. If this is not done the tank remains under pressure and check valve 25, of compressed air system 18, blocks the passage of aqueous solution from tank 4 to compressor's 6 diaphragm. To depressurize ESD 1 for refilling or for emptying tank 4 through port 47, pressure release valve 87, of pressure release system 15, is opened. Valve 87 also allows for rapid release and for back automatic return of preset pressure on aqueous solution systems 16 or 17 after refilling tank 4.

Having described and illustrated the principles of the invention in a preferred embodiment thereof, it should be apparent that the invention can be modified in arrangement and detail without departing from such principles. I claim all modifications and variation coming within the spirit and scope of the following claims.

I claim:

1. A method of applying a biological control system to a target crop in an active use zone, which comprises providing a bio-carrier system including at least one active biological control agent comprising any one of adult insects, insect larva and insect eggs, a soluble cellulose-containing compound and water which is non-toxic with respect to said active biological control agent;

combining the soluble cellulose-containing compound, the biological control agent and water to form said biological control system;

transporting said bio-carrier through the atmosphere toward the active use zone while maintaining the biological control agent in an active state;

delivering said bio-carrier system to, and depositing said bio-carrier system in, said active use zone while maintaining the biological control agent in an active state;

adhering the biological control agent in the active use zone while maintaining the biological control agent in an active state; and maintaining the biological control agents in an active state in said active use zone without being substantially inhibited by the adhesive properties of the soluble cellulose-containing compound thereby permitting said active biological control agents to protect said target crop from attack by harmful pests and predators which would harm or destroy said target crop.

2. The method of claim 1, which includes the step of spraying said bio-carrier system into said active use zone.

3. The method of claim 1, wherein said active biological control agents comprise arachnids.

4. The method of claim 1, wherein said soluble cellulose-containing compound is selected from a group consisting of carboxymethyl cellulose, hydroxyethyl cellulose, hydroxypropyl cellulose, hydroxy cellulose, and methyl cellulose.

5. The method of claim 1, which includes the further step of adding to the bio-carrier system a preservative for increasing the shelf life of the soluble cellulose-containing compound.

6. The method of claim 5, wherein said preservative material comprises methyl perecept or sodium benzoate.

7. The method of claim 1, wherein said target crops are grown above ground level, and said soluble cellulose-containing compound prevents said active biological control agents from falling or being blown to the ground when said bio-carrier system is transported through the atmosphere.

8. The method of claim 7, which includes the step of spraying said bio-carrier above ground level while maintaining the biological control agents in an active state.

9. A method for forming a biological control system for application to a target crop in an active use zone, which comprises the steps of providing a bio-carrier system including at least one active biological control agent comprising any one of adult insects, insect larva and insect eggs, a soluble cellulose-containing compound and water which is non-toxic with respect to said active biological control agent, said soluble cellulose-containing compound acting as a carrier for transporting said active biological control agent through the atmosphere while maintaining the biological control agent in an active state, and for delivering, depositing and adhering the biological control agent in the area of the target crop while maintaining said biological control agents in an active state, said active biological control agents being employed to protect said target crop from attack by harmful pests and predators which would harm or destroy said target crop in said active use zone; and combining the soluble cellulose compound, the biological control agent and water to form said biological control system.

10. The method of claim 9, which includes the step of providing a bio-carrier system which can be sprayed into said active use zone while maintaining the biological control agent in an active state.

11. The method of claim 9, wherein said active biological control agents comprise arachnids.

12. The method of claim 9, wherein said soluble cellulose-containing compound is selected from a group consisting of carboxymethyl cellulose, hydroxyethyl cellulose, hydroxypropyl cellulose, hydroxy cellulose, and methyl cellulose.

13. The method of claim 9, which includes the further step of adding to the bio-carrier system a preservative for increasing the shelf life of the soluble cellulose-containing compound.

14. The method of claim 13, wherein said preservative material comprises methyl perecept or sodium benzoate.

15. The method of claim 9, wherein said target crops are grown above ground level, and when said bio-carrier system is transported through the atmosphere, said soluble cellulose-containing compound prevents said active biological control agents from falling or being blown to the ground.

16. The method of claim 15, wherein said bio-carrier system is transported by spraying said bio-carrier above ground level and the biological control agents are maintained in an active state.

17. A method for forming a biological control system for application to a target crop in an active use zone, which comprises the steps of providing a concentrated bio-carrier system including at least one active biological control agent comprising any one of adult insects, insect larva and insect eggs, a soluble cellulose-containing compound and water which is non-toxic with respect to said active biological control agent, said soluble cellulose-containing compound acting as a carrier for transporting said active biological control agent through the atmosphere while maintaining the biological control agent in an active state, and for delivering, depositing and adhering the biological control agent in the area of the target crop while maintaining said biological control agents in an active state, said active biological control agents being employed to protect said target crop from attack by harmful pests and predators which would harm or destroy said target crop in said active use zone; and combining the soluble cellulose compound, the biological control agent and water to form said concentrated biological control system.

* * * * *